(12) United States Patent
Perlman et al.

(10) Patent No.: US 7,866,908 B2
(45) Date of Patent: *Jan. 11, 2011

(54) STETHOSCOPE CLEANING ASSEMBLY

(76) Inventors: Michael Perlman, 2210 SW. 102 Dr., Davie, FL (US) 33324; James M. Sellers, 2100 N. Ocean Blvd., #501, Ft. Lauderdale, FL (US) 33305; Keith Rubin, 2100 N. Ocean Blvd., #501, Fort Lauderdale, FL (US) 33305; Mathew Cardinali, 2100 N. Ocean Blvd., #501, Ft. Lauderdale, FL (US) 33305; Michael R. Cole, 2100 N. Ocean Blvd., #501, Fort Lauderdale, FL (US) 33305; Sidney Perlman, 1500 S. Ocean Blvd., Apt. 1102 South, Boca Raton, FL (US) 33432

( * ) Notice: Subject to any disclaimer, the term of this patent is extended or adjusted under 35 U.S.C. 154(b) by 0 days.

This patent is subject to a terminal disclaimer.

(21) Appl. No.: 12/316,123

(22) Filed: Dec. 9, 2008

(65) Prior Publication Data

US 2009/0144918 A1 Jun. 11, 2009

Related U.S. Application Data

(63) Continuation-in-part of application No. 12/079,077, filed on Mar. 24, 2008, now Pat. No. 7,503,335, which is a continuation-in-part of application No. 11/728,207, filed on Mar. 23, 2007, now Pat. No. 7,406,973.

(51) Int. Cl.
| | |
|---|---|
| *B43K 29/00* | (2006.01) |
| *B43K 1/00* | (2006.01) |
| *B05C 1/00* | (2006.01) |
| *A47L 13/12* | (2006.01) |
| *A47L 1/08* | (2006.01) |
| *A47L 1/02* | (2006.01) |
| *B08B 9/00* | (2006.01) |
| *B08B 3/12* | (2006.01) |
| *A61B 7/02* | (2006.01) |
| *A61L 2/00* | (2006.01) |
| *A61L 9/00* | (2006.01) |

(52) U.S. Cl. ............... 401/193; 401/17; 401/22; 401/27; 401/195; 401/292; 15/97.1; 134/166 R; 134/167 R; 134/168 R; 134/172; 134/197; 181/131; 422/292; 422/300

(58) Field of Classification Search ............. 401/9, 401/17, 22, 27, 136, 193, 195, 292; 15/97.1, 15/1, 229.11; 134/166 R, 167 R, 168 R, 134/172–179, 184, 187, 191–193, 201, 195–197; 181/131; 250/455.11; 422/28, 292, 300

See application file for complete search history.

(56) References Cited

U.S. PATENT DOCUMENTS 4,210,974 A * 7/1980 Stoltzman ............... 15/21.2

(Continued)

FOREIGN PATENT DOCUMENTS

| WO | WO 02/094326 A1 | 11/2002 |
| WO | WO 2008/118311 A2 | 10/2008 |
| WO | WO 2008/118401 A2 | 10/2008 |

OTHER PUBLICATIONS

Dix, et al., "Environmental Surface Cleaning First Defense Against Infectious Agents." http://www.vpico.com/articlemanager/printerfriendly.aspx?article=60960; Dec. 2, 2006; 7pg.

(Continued)

*Primary Examiner*—Gregory L Huson
*Assistant Examiner*—Ryan A Varnum
(74) *Attorney, Agent, or Firm*—Malloy & Malloy, P.A.

(57) ABSTRACT

An assembly structured to clean the head portion of a stethoscope comprising a housing including a path of travel along which the head portion passes during cleaning. A supply of cleaning fluid is associated with a dispenser assembly which is cooperatively disposed relative to an activating assembly. The activating assembly is manually operated due to moveable engagement with the head portion as it travels along the path of travel. The activating assembly is thereby operatively positioned to activate the dispenser assembly when engaged by the head portion as it passes along the path of travel. The dispenser assembly delivers the cleaning fluid to an applicator assembly which distributes the cleaning fluid to the head portion and facilitates the cleaning thereof and removal of excess cleaning fluid there from.

27 Claims, 17 Drawing Sheets

U.S. PATENT DOCUMENTS

| | | | |
|---|---|---|---|
| 4,449,976 A | | 5/1984 | Kamen |
| 4,701,968 A | * | 10/1987 | Stoltzman .................. 15/21.2 |
| 4,953,999 A | * | 9/1990 | Rivers ......................... 401/9 |
| 5,048,549 A | | 9/1991 | Hethcoat |
| 5,114,670 A | | 5/1992 | Duffey |
| 5,185,532 A | | 2/1993 | Zabsky et al. |
| D375,161 S | | 10/1996 | Hart |
| 5,641,464 A | | 6/1997 | Briggs, III et al. |
| 5,692,657 A | | 12/1997 | Kilo et al. |
| 5,865,551 A | | 2/1999 | Lalli et al. |
| 5,892,233 A | | 4/1999 | Clement |
| 5,925,021 A | * | 7/1999 | Castellano et al. .......... 604/207 |
| 6,018,835 A | | 2/2000 | Schonfeld |
| D425,353 S | | 5/2000 | Foy |
| D445,185 S | | 7/2001 | Najmi |
| 6,484,918 B1 | | 11/2002 | Lefebvre |
| 6,575,917 B2 | | 6/2003 | Giroux et al. |
| 7,258,125 B2 | | 8/2007 | Holbrook |
| 7,282,186 B2 | | 10/2007 | Lake, Jr. et al. |
| 7,406,973 B1 | | 8/2008 | Perlman et al. |
| 7,503,335 B2 | | 3/2009 | Perlman et al. |
| 2002/0146343 A1 | | 10/2002 | Jenkins et al. |
| 2002/0198564 A1 | | 12/2002 | Pichon et al. |
| 2004/0258560 A1 | | 12/2004 | Lake, Jr. et al. |
| 2005/0214185 A1 | | 9/2005 | Castaneda |
| 2005/0236579 A1 | | 10/2005 | Jenkins et al. |
| 2005/0254992 A1 | | 11/2005 | Jenkins et al. |
| 2007/0080017 A1 | | 4/2007 | Stickley |
| 2007/0256753 A1 | | 11/2007 | Riley |

OTHER PUBLICATIONS

Virgo Publishing., "A Clean Sweep: Surface Cleaning in the Healthcare Environment." http://www.vpico.com/article-manager/printerfriendly.aspx?article=60253; Dec. 1, 2004; 3 pg.

McCaughey., "Coming Clean—New York Times." http://www.nytimes.com/2005/06/06/opinion/06mccaughey.html?ei=5088&en=d591e517f . . . ; Dec. 2, 2006; 1 pg.

Sharmila et al., "Stethoscope and Nosocomial Infection," Indian Journal of Pediatrics, 2000; 67 (3): 197-199.

Marinella, et al., "The Stethoscopy: A Potential Source of Nosocomial Infection?," vol. 157(7), Apr. 14, 1997, pp. 786-790, Mar. 30, 2006.

Jones, et al., "Stethoscopes: A Potential Vector of Infection?" Annals of Emergency Medicine. 26:Sep. 3, 1995; 296-299.

CDC, "Contact Precautions from the Guidelines for Isolation Precautions in Hospitals (Jan. 1996)." http://www.cdc.gov/ncidod/dhqp/gl_isolation_contact.html; Dec. 2, 2006; 2 pg.

CDC, "Standard Precautions from the Guidelines for Isolation Precautions in Hospitals (Jan. 1996)." http://www.cdc.gov/ncidod/dhqp/gl_isolation_standar.html; Dec. 2, 2006; 2 pg.

Schneider, "Report of the Counsil on Science and Public Health—CSAPH's Sunet Review of 1996 House Policies".

"American Medical AssociationProceedings of the House of Delegates," 50th Interim Meeting, Dec. 8-11, 1996. Resolution 501. Policy H-440. 908.

* cited by examiner

STETHOSCOPE CLEANING ASSEMBLY

CLAIM OF PRIORITY

The present application is a Continuation-In-Part application of previously filed, application having Ser. No. 12/079,077 filed on Mar. 24, 2008, now U.S. Pat. No. 7,503,335 which is a Continuation-In-Part of U.S. patent application having Ser. No. 11/728,207, filed on Mar. 23, 2007, which matured into U.S. Pat. No. 7,406,973 on Aug. 5, 2008, all of which are incorporated herein in their entirety by reference.

BACKGROUND OF THE INVENTION

1. Field of the Invention

This invention is directed to an assembly structured to clean the head portion of a stethoscope comprising a housing including a path of travel along which the head portion passes during cleaning. A supply of cleaning fluid is associated with a dispenser assembly which is cooperatively disposed relative to an activating assembly. The activating assembly is operatively positioned to activate the dispenser assembly when engaged by the head portion as it passes along the path of travel. The dispenser assembly delivers the cleaning fluid to an applicator assembly or at least to an area communicating with the applicator assembly, which distributes the cleaning fluid to the head portion and facilitates the cleaning thereof and removal of excess cleaning fluid there from.

2. Description of the Related Art

As is well recognized in the medical profession and commonly acknowledged by many individuals not directly associated with the medical care industry, the use of a stethoscope by health care providers is routine. As typically applied, the head and/or diaphragm portion of the stethoscope is normally placed in direct contact with the skin of the patient at various locations over the patient's body. In applying the stethoscope in this manner and in particular in situations where the stethoscope head or diaphragm may be exposed to the bodily fluids of the patient, the transmission of infection from patient to patient is a distinct possibility.

While some stethoscopes are structured for disposal after each use, a great number of stethoscope instruments are non-disposable and are intended for continued and repeated use. This latter category of stethoscopes are typically carried by the health care provider on a substantially continuous basis and used repeatedly for examination of multiple patients. In order to avoid the transmission of infection from patient to patient when using this latter category of instruments, attempts have been made to facilitate at least a minimal cleaning and/or disinfecting of the head portion of the stethoscope. However, because of time demands, emergency situations and other situations which frequently occur, a health care provider may only perform a minimal cleaning of the instrument on an occasional basis. Such cursory cleaning procedures may involve a physical wiping of the head and diaphragm portions of the stethoscope with some type of disinfecting or cleaning material wipe. Although, these cursory cleaning procedures may be effective, they are burdensome, time consuming and require the ready availability of these wipes. Furthermore, while available and inexpensive, these wipes have generally not been integrated into routine physician practice.

In order to overcome problems of the type set forth above, attempts have been made to develop various types of cleaning devices and/or systems which are intended to provide a more thorough, effective cleaning of at least the head and/or diaphragm portions of the stethoscope. However, many known or conventional devices, while being at least minimally operative to accomplish their intended purpose, also suffer from numerous disadvantages. Such disadvantages generally relate to accomplishing an effective cleaning, disinfecting or possible sterilization of the instrument and the fact that many of such known cleaning devices are difficult or too time consuming for convenient use.

To better appreciate the requirements necessary to accomplish a proper cleaning and disinfecting of the stethoscope head, it is important to understand the various structural components thereof and their intended use during an examination procedure. More specifically, the stethoscope head typically includes a diaphragm portion comprising a thin disk of appropriate material that is disposed in confronting relation to a patient's skin. As such, the diaphragm forms an acoustical seal with the contacted portion of the patient. In addition, the head portion also includes a ring or rim which retains or is otherwise disposed and structured for supportive engagement with the diaphragm. Finally, the stethoscope head includes a base or spine of the head formed of metal or other composite base material that is structured to serve as the location where the user may grasp the device comfortably, usually with a thumb and one or two fingers of a single hand. A magnification and transmission of the sounds detected during the examination procedure is thereby accomplished. In addition, an appropriate conduit or tubing which may be formed of a rubber or like material is secured to the head and extends outwardly there from so as to interconnect the ear pieces of the stethoscope to the head portion.

Health care associated (nosocomial) infections are a growing concern for hospitals in the United States and worldwide. Approximately, two million patients admitted to U.S. hospitals each year acquire a health care associated infection. Of these, more than seventy thousand will die. These infections add about $30 billion annually to U.S. healthcare cost.

The transfer of pathogenic bacteria from one patient to another is a major cause of healthcare associated infections. This transfer may be facilitated by healthcare workers who do not adequately clean and disinfect their hands and/or patient-care equipment after patient contact.

Stethoscopes harbor pathogenic bacteria. Bacteria may be transferred to intact human skin directly from a stethoscope diaphragm. Stethoscope diaphragm and rim (the portions of the stethoscope that directly contact the patient's skin) may be adequately disinfected and cleaned by one or several wipes with a prepackaged isopropyl alcohol pad or swab. However, the majority of healthcare workers do not clean or disinfect their stethoscope after each patient encounter. Less than half of workers clean their stethoscopes daily or even weekly. Common reasons for not cleaning or disinfecting stethoscopes are that the alcohol pads and swabs are not readily available, are messy, time consuming to use and require disposal.

The Centers for Disease Control and Prevention recommends that healthcare workers dedicate the use of non-critical care equipment to a single patient. If this is not possible, then it is recommended that these items be adequately cleaned and disinfected before being used on another patient. These recommendations are specifically for patients that are known or suspected to harbor pathogenic organisms. However, the Centers for Disease Control and Prevention also recommends that for all patients receiving care in a hospital, an item of patient care equipment must not be reused on another patient until it has been cleaned and reprocessed appropriately. The American Medical Association has also resolved that healthcare providers should frequently clean their stethoscopes to prevent the spread of nosocomial infections.

Accordingly, there is a need for a device that allows healthcare providers to rapidly and safely clean and disinfect their stethoscope diaphragm and rim before and after examining a patient. Such a proposed device should be located conveniently in the patient's room or examination area and preferably be wall mounted. Moreover such a proposed cleaning assembly should be preferably structured to facilitate a single, rapid swipe through the proposed device by a stethoscope operator so as to adequately clean and disinfect the stethoscope diaphragm and rim. These are the elements of a stethoscope that come in contact with a patient and are an important potential source of nosocomial infections. Accordingly, a proposed invention should provide a novel, inexpensive, safe, convenient and time efficient solution to the potential stethoscope-to-patient transmission of infectious agents such as viruses, bacteria and fungi.

It will be preferable if a proposed stethoscope cleaning and disinfecting device had the following additional features in order to overcome disadvantages and problems recognized with prior art or conventional cleaning devices. The proposed device should safely enclose the disinfecting agent to prevent spillage and dissuade tampering. After cleaning and disinfecting the stethoscope's diaphragm and rim, the device should remove excess disinfecting agent so as to not leave an excessive amount of this agent on the diaphragm or rim.

Further, any such cleaning device that is located in a patient's room or in an examination area may, over time, have its exterior surface contaminated by pathogenic bacteria. Therefore, it is essential that to prevent further spread of pathogenic bacteria, a proposed device should allow the operator to avoid touching the device with his or her hands during the stethoscope cleaning and disinfecting procedure.

In light of the above, there is a long standing and well recognized need in the medical profession for a cleaning assembly and an attendant procedure which effectively, quickly and reliably serve to clean and disinfect the head portion and/or at least the exposed diaphragm and supportive rim thereof. Such a proposed cleaning assembly should be structured to effectively isolate at least the diaphragm of the head portion from the surrounding environment during the cleaning procedure. In addition a proposed cleaning assembly should be structured to apply, clean and remove excess cleaning fluid from the diaphragm and/or other adjacent or contiguous components of the head portion.

As set forth above, an improved cleaning assembly should be capable of effectively isolating the diaphragm and similarly exposed portions of the head of the stethoscope and segregate the hands of the user from the cleaning area of the proposed cleaning assembly. As such, a cleaning procedure associated with the proposed cleaning assembly should occur on the interior of an appropriately structured and dimensioned housing. An appropriate housing of the proposed cleaning assembly should also prevent excessive fluid from escaping and eliminate the possibility of the hand of the user contaminating the diaphragm and/or rim during the cleaning procedure.

Finally, such a proposed cleaning assembly should be relatively simple in operation and structure and also include components that facilitate the replacement of the intended cleaning fluid and any non-durable elements without undue interference with the remaining operative components associated with the proposed cleaning assembly. Further, a proposed assembly of this type to be described in greater detail hereinafter may include additional preferred embodiments comprising replaceable components of varying function. These replaceable components may preferably include, but not be limited to, a receptacle or sump, portions of the applicator assembly including, but not limited to, an applicator member, a cleaning member and a member that removes excess cleaning fluid from the portions of the stethoscope to which the cleaning fluid is applied. All of the above components may be of durable or nondurable materials. The ability to replace at least some of these components as a single combined and/or interconnected unit facilitates the ease of use and versatility of the proposed cleaning assembly.

A further useful, novel and unique feature of the various replaceable components of the proposed cleaning assembly relate to an appropriately structured and disposed indicator assembly which may include a floating level indicator and/or a window or appropriate viewing structure formed in the housing. Moreover, the indicator assembly and the various proposed components associated therewith will function to apprise the user when the cleaning fluid needs to be replaced.

As such, a proposed cleaning assembly of the type set forth in greater detail hereinafter, should be capable of a long operable life even when exposed to continuous use and a relatively harsh working environment.

SUMMARY OF THE INVENTION

The present invention is directed to a cleaning assembly structured to clean a head portion, including at least an exposed diaphragm and supporting rim of the stethoscope, as well as other exposed portions which come into contact with a patient's body. As generally used, it is recognized that the terms "clean" and/or "disinfect" may be strictly interpreted as referring to different procedures intended to accomplish different results. By way of example, the term "clean" and "cleanse" may be typically used in situations where it is intended to remove dirt, impurities, debris, contaminants, etc. In contrast, the term "disinfect" may be used to remove or kill harmful microorganisms or render them harmless. However, as used herein the terms "clean", "cleanse" and/or "cleaning action" are meant to encompass all of the above cleaning and disinfecting procedures. The category or degree of "cleaning" in a practical application of the present invention will be at least partially dependent on the cleaning fluid to which the head portion of the stethoscope is exposed.

By way of example, a most preferred embodiment of the present invention may incorporate the use of a cleaning fluid comprising an alcohol based composition. More specifically, the cleaning fluid used in the operation of the present invention may include, but is not limited to, an antimicrobial fluid. Moreover, the cleaning fluid is applied in an appropriate manner to the exposed surfaces of the diaphragm, supportive rim and possibly other adjacent or contiguous portions associated with the head portion of the stethoscope. Therefore, other factors to be considered are the type of wiping, scrubbing, brushing or other types of physical engagement or contact to which the head portion is subjected during the cleaning procedure. Accordingly, with the above acknowledgement to the strict definitions of the above terms, the use of the term "clean", "cleaning", and/or "cleaning action" are also meant to encompass all of the above noted procedures, the various types of cleaning fluids capable of being used as well as any of a variety of different types of physical engagement or contact applied to the portions of the head of the stethoscope being treated.

Therefore, the cleaning assembly of the present invention comprises a housing including an at least partially hollow interior of sufficient dimension and configuration to include various other operative components of the cleaning assembly therein. More specifically, the housing includes an entrance portion and an exit portion disposed in spaced relation to one another. The entrance and exit are respectively dimensioned and configured to facilitate the entering of the head portion of the stethoscope and the removal thereof from the interior of the housing. Further, the housing includes a path of travel extending between and disposed in communicating relation with both the entrance and exit portions. Moreover, the entrance, exit and path of travel are cooperatively disposed and structured to facilitate movement or passage of the head portion along the path of travel at least partially on the interior of the housing.

When the head portion is passing along the path of travel, the diaphragm, supporting rim and other contiguous parts of the head portion are segregated from the exterior of the housing and ambient conditions associated therewith. It is further emphasized that in order to increase the efficiency and effectiveness of the cleaning procedure, the housing as well as the path of travel and other components to be described in greater detail hereinafter are selectively structured, disposed and dimensioned so as to facilitate passage of the head along the path of travel and between the entrance and exit portions by means of a single "swiping" action. Such a swiping action eliminates the requirement or need for a successive, reciprocal or repetitive type of movement of the head portion on the interior of the housing and along the path of travel in order to accomplish an effective cleaning thereof as intended.

Additional structural and operative features of the present invention include a fluid supply mounted on the interior of the housing and comprising at least one but, in other preferred embodiments, a plurality of fluid reservoirs. Each of the one or more fluid reservoirs is structured to contain a "cleaning" fluid disposed therein. Further, each of the fluid reservoirs is associated with a dispenser assembly preferably, but not exclusively, defined by a pump assembly. Each pump assembly associated with each of the fluid reservoirs is, in at least one preferred embodiment of the present invention, mechanically or otherwise forcibly operated at least partially concurrently to the passage of the head portion of the stethoscope along the aforementioned path of travel. In addition an indicator assembly is associated with the fluid supply and/or at least one of the fluid reservoirs. Such an indicator assembly may take the form of a window and/or associated float structure disposed and structured to facilitate an accurate determination of the existing quantity of cleaning fluid remaining in the cleaning fluid supply.

In order to effectively dispense the cleaning fluid from each of the one or more fluid reservoirs, the present invention also includes an activating assembly disposed within the housing and movable between an initial position and an operative position. As such, the activating assembly includes at least one but more practically, a plurality of activating members preferably, but not necessarily, corresponding in number to the number of fluid reservoirs and associated dispenser assemblies, as set forth above.

In a most preferred embodiment of the present invention the versatility, safety and efficiency of the cleaning assembly is further demonstrated by the elimination of the need for any supplemental power. Supplemental power, in the form of an electrically driven motor, has been employed in other devices with a similar purpose. The use of an electrically driven motor poses to the user the risks of malfunction, fire, electrical shock or explosion. The risk of fire and explosion are even greater when considering that the vast majority of preferred cleaning fluids for equipment cleaning are alcohol based and flammable. Other known cleaning assemblies, while not employing a motor or flammable cleaning fluid, do utilize high voltage electricity (200-1,000 volts), which exposes the user to the risk of electrocution. Also, known devices of this type pose a risk of UV light exposure to the user or others in the vicinity of the device, when in use.

Moreover, the cooperative positioning and structuring of the various operative components of the cleaning assembly provide for the dispenser and application of the cleaning fluid from the one or more fluid reservoirs onto an applicator assembly and from the applicator assembly on to the diaphragm, rim and other surfaces or parts of the head portion intended to be cleaned. Further, the force required to physically pass the head portion along the aforementioned path of travel will result in the dispenser of the cleaning fluid from the one or more reservoirs. More specifically, the activating assembly, including the one or more activating members, originally assumes an initial position. Such initial position comprises the one or more activating members disposed in interruptive relation to the path of travel and more specifically to the head portion as it travels along the path of travel. As such, the head portion, during such passage will engage and drivingly force each of the one or more activating members from the initial position to their respective operative positions. Accordingly, the operative position of each of the activating members comprises their driving, activating or operating disposition relative to each of the dispenser assemblies associated with respective ones of the fluid reservoirs. As set forth above, the dispenser assemblies may preferably include a mechanical or otherwise forcibly driven pump mechanism. Therefore, each of the activating members and possibly mechanical linkage associated therewith serve to appropriately operate the pump assemblies so as to dispense the cleaning fluid onto an applicator assembly for distribution onto the appropriate portions of the head of the stethoscope.

Moreover, the applicator assembly is disposed and structured to apply cleaning fluid to the diaphragm and other appropriate portions of the head of the stethoscope, which contact the applicator assembly as the head of the stethoscope passes along the path of travel. The applicator assembly is also disposed and structured to provide a cleaning and possibly a mildly abrasive or scrubbing action to the head portion and in at least some preferred embodiments, remove excess cleaning fluid therefrom. The above set forth cleaning procedure is accomplished on the interior of the housing prior to removal of the head portion through the aforementioned exit. In addition, the applicator assembly, in at least some of the embodiments of the present invention, may be removably mounted on the interior of the housing, as part of a removable, replaceable cartridge, so as to facilitate replacement and/or maintenance thereof when needed.

Accordingly, the structural and operative features of the cleaning assembly of the present invention allow for the utilization of a single swiping action which is unique and distinguishable from known or conventional stethoscope cleaning assemblies. Moreover, in a single, smooth, one-handed, unidirectional swiping maneuver, the operator brings the stethoscope head into the interior chamber of the housing of the device. In the same swiping maneuver, the operator brings the stethoscope head in contact with the one or more activating members thereby forcibly driving the one or more activating members into an operative position to actively dispense cleaning fluid onto the aforementioned applicator assembly. In the same swiping maneuver, the operator brings the diaphragm and rim portions of the stethoscope head into operative contact with the various components of the applicator assembly. This serves to distribute cleaning fluid across the diaphragm and rim in such a manner as to clean the diaphragm and rim. In the same swiping maneuver, the operator brings the diaphragm and rim portions of the stethoscope head into activating contact with a cleaning member of the applicator assembly, which serves to remove dirt, debris and contaminants from the stethoscope diaphragm and rim, and distributes the cleaning solution over the rim and diaphragm. In the same swiping maneuver, the operator brings the diaphragm and rim portions of the stethoscope head into activating contact with an additional member of the applicator assembly that serves to remove excess cleaning fluid, thereby at least partially drying the diaphragm and rim. In the same swiping maneuver, the operator brings the stethoscope head further along the path of travel until it exits the interior chamber of the housing. The end result of this single, smooth, one-handed, unidirectional swiping maneuver is a disinfected, cleaned and at least partially dried diaphragm and rim of the stethoscope head.

Accordingly, the structural and operative features of the stethoscope cleaning assembly of the present invention overcome many if not all of the disadvantages of known or conventional devices. More specifically, such conventional devices typically require the use of two hands, one to hold the stethoscope and the other to depress or push an activating structure on the conventional cleaning devices. Any lever or button located externally to a conventional cleaning device may become infected or contaminated by the external environment. If a user touches an external lever or button with a hand, the user's hand may become infected or contaminated with potentially dangerous microorganisms located on the lever or button. The present invention avoids this potential serious contamination risk by the elimination of any external activating buttons, levers or like members. Yet other conventional or known cleaning assemblies require a separate wiping maneuver to dry the stethoscope head on a pad external to the device. An external pad is less advantageous in that this pad is also susceptible to infection and contamination by the external environment. This infection and contamination may be spread to the user's stethoscope during the drying maneuver. The present invention, which lacks an external pad or like structure avoids this potentially serious contamination risk.

Therefore, the cleaning assembly of the present invention comprises structural and operative features which facilitate the cleaning, and/or disinfecting of the diaphragm, rim and other appropriate portions of the head of the stethoscope in a quick, effective and reliable manner so as to overcome many of the disadvantages and problems associated with known or conventional cleaning assemblies intended for this purpose.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 10:
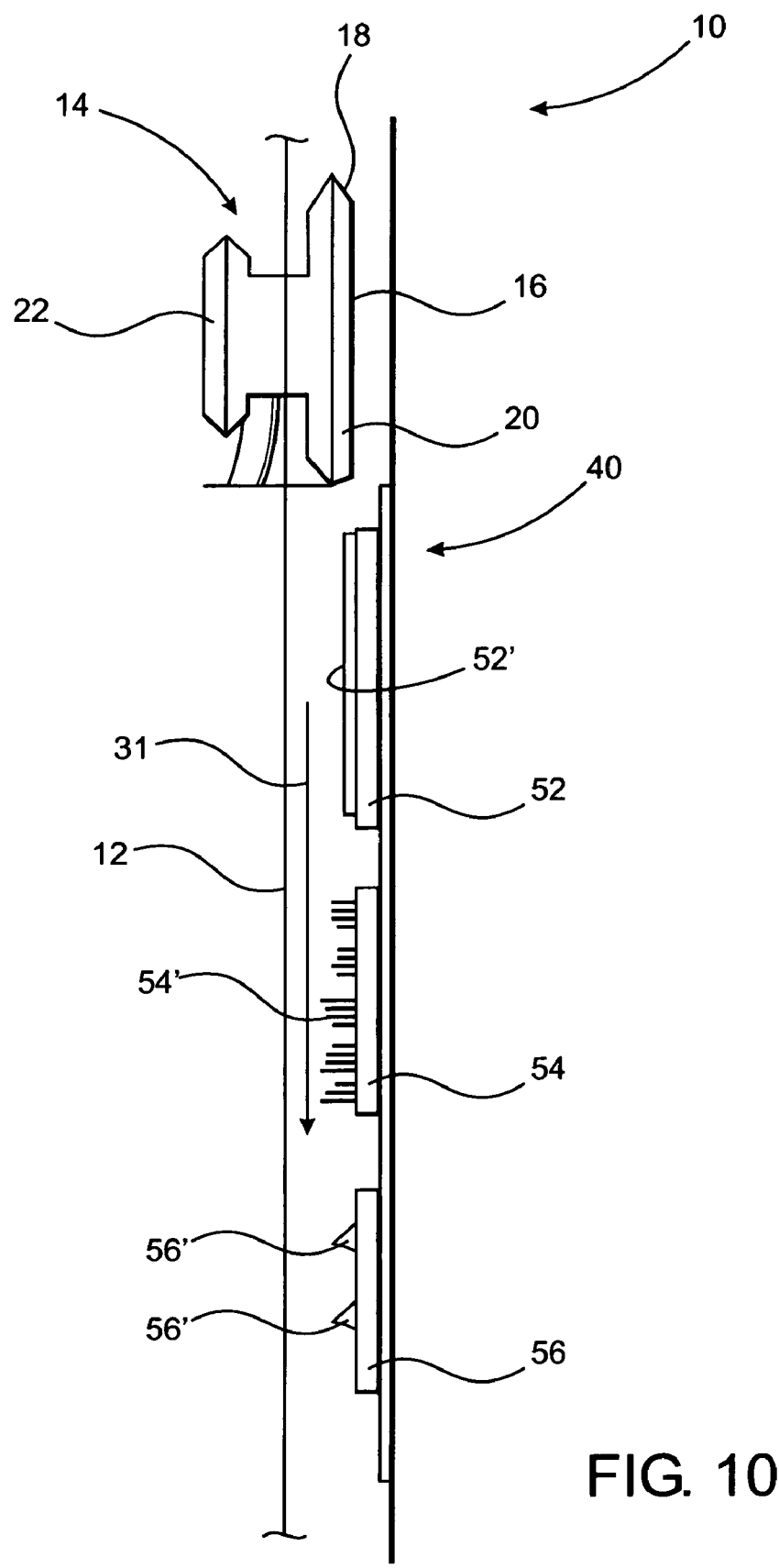
FIG. 10 is a schematic view of the embodiment of at least one preferred embodiment of the present invention in partial schematic form, wherein the head portion of the stethoscope is disposed for cleaning and various operative components of an applicator assembly are disposed in an operative position.

As shown in the accompanying drawings, the present invention is directed to a cleaning assembly 10 for the head of a stethoscope. The cleaning assembly 10 includes a housing 12 having a hollow interior of sufficient dimension and configuration to contain a plurality of operative components to be described in greater detail hereinafter. As also described, the cleaning assembly 10 is specifically structured to "clean" the diaphragm, supportive rim and other exposed portions of the head which are brought into direct contact with a patient's body. More specifically, the head portion 14 as represented in FIG. 10 includes a diaphragm 16 and supportive and/or surrounding rim portion 18 generally associated with an exposed face or patient contacting portion 20 of the stethoscope head 14. Additional features relating to the manipulation or placement of the head 14 comprise the structuring of the housing 12, as well as other operative components associated therewith, which facilitates a user grasping of the spine or stem portion 22 located on the exterior of the housing 12 with a single hand during the cleaning procedure. As such, the cleaning of the head 14 can be effectively accomplished by the user performing a single, unidirectional, one-handed "swiping" motion of the head 14 causing it to pass on the interior of the housing 12 and along a predetermined path of travel, as at 30, 31, explained in greater detail hereinafter.

Figure 1:
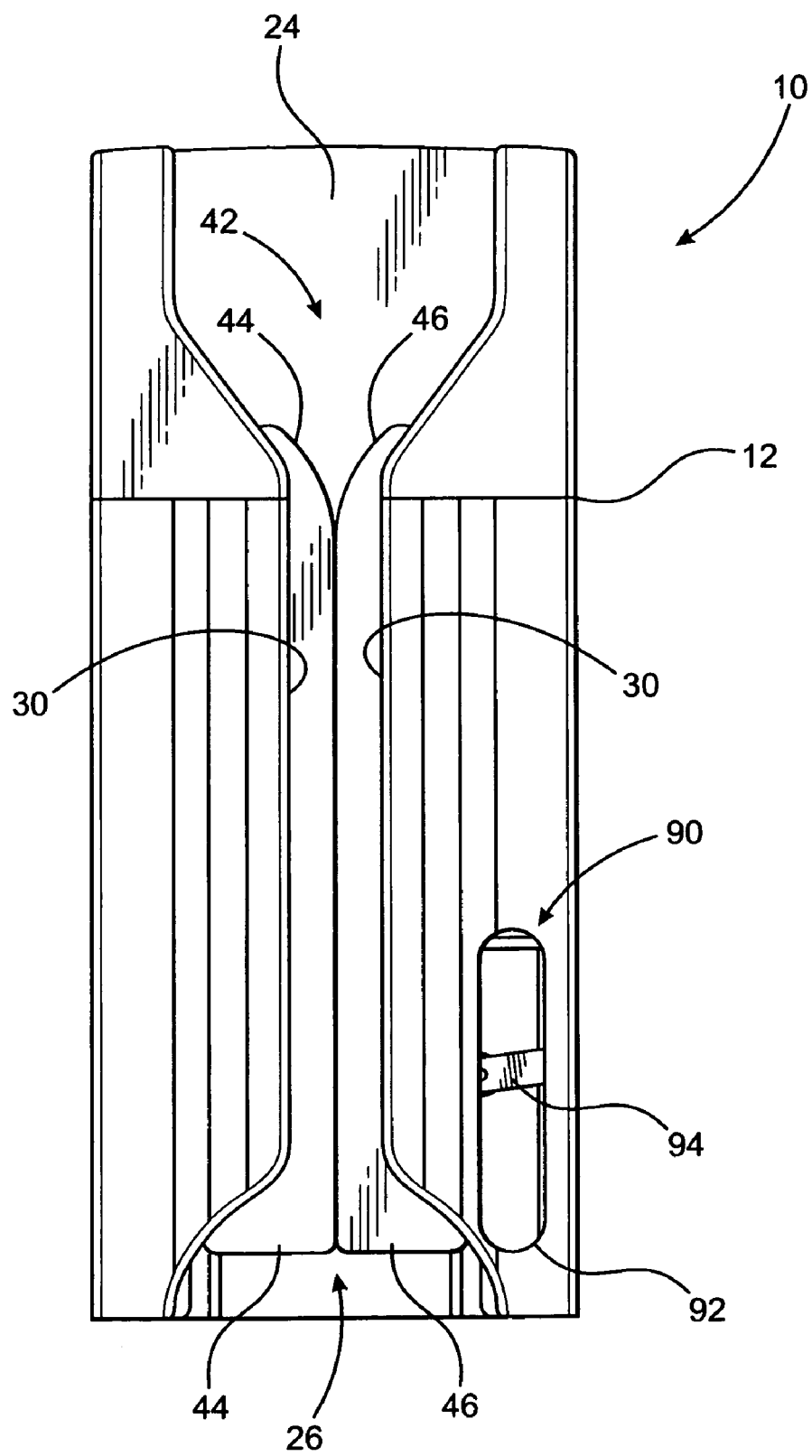
FIG. 1 is a front view in partial schematic form of a cleaning assembly of the present invention wherein the various operative components thereof are in an initial and/or non-activating position.
Figure 2:
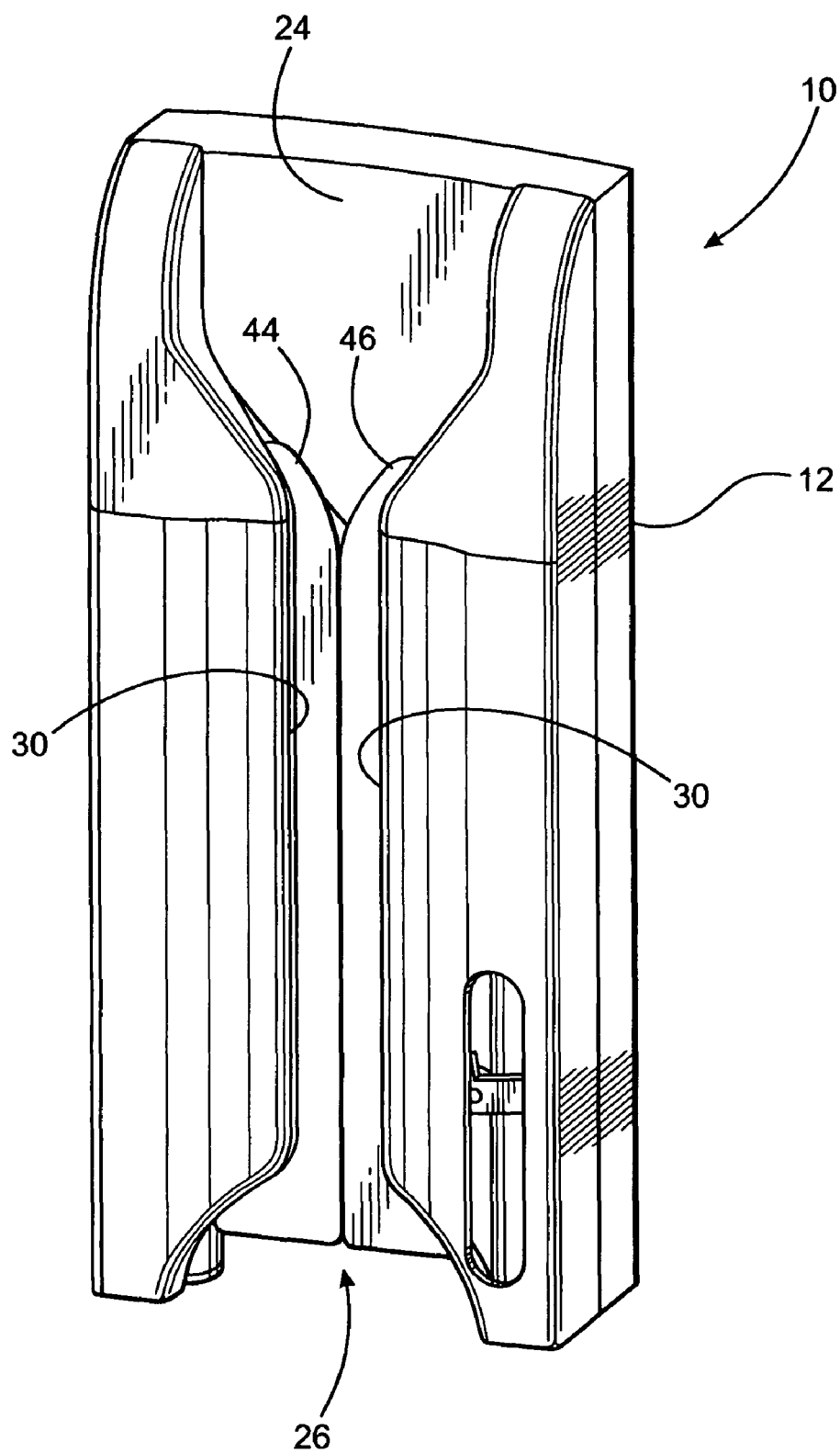
FIG. 2 is an exterior perspective view of the preferred embodiment of FIG. 1 of the cleaning assembly of the present invention.

With primary reference to FIGS. 1 and 2, the housing 12 includes an entrance portion 24 and an exit portion 26 respectively defined by openings in one face or surface of the housing 12. The entrance and exit openings 24 and 26 are dimensioned and configured to facilitate the passage of the head portion 14 respectively into and out of the interior of the housing 12. In addition, the housing 12 further includes the aforementioned path of travel of the head portion 14, which is at least partially defined by an elongated channel 30, disposed between and in communication with both the entrance 24 and exit 26. Further, the longitudinal dimension of the path of travel and/or open channel 30 is such as to facilitate travel or passage of the head portion 14 into cooperative relation with the various operative components which perform the cleansing procedure as set also forth in greater detail hereinafter.

Similarly, the transverse dimension or width of the channel 30 facilitates passage of the head portion 14 along the path of travel in a manner which at least partially segregates the spine or stem 22, being gripped by a single hand of the user, on the exterior of the housing 12. As such, the user will not be exposed or have ready access to the interior path of travel within the housing 12 and the various operative components of the assembly 10. Further, the dispensing of a cleaning fluid and the application of that cleaning fluid to the diaphragm 16 and other appropriate surface portions of the head 14 is substantially retained on the interior of the housing 12.

Figure 3:
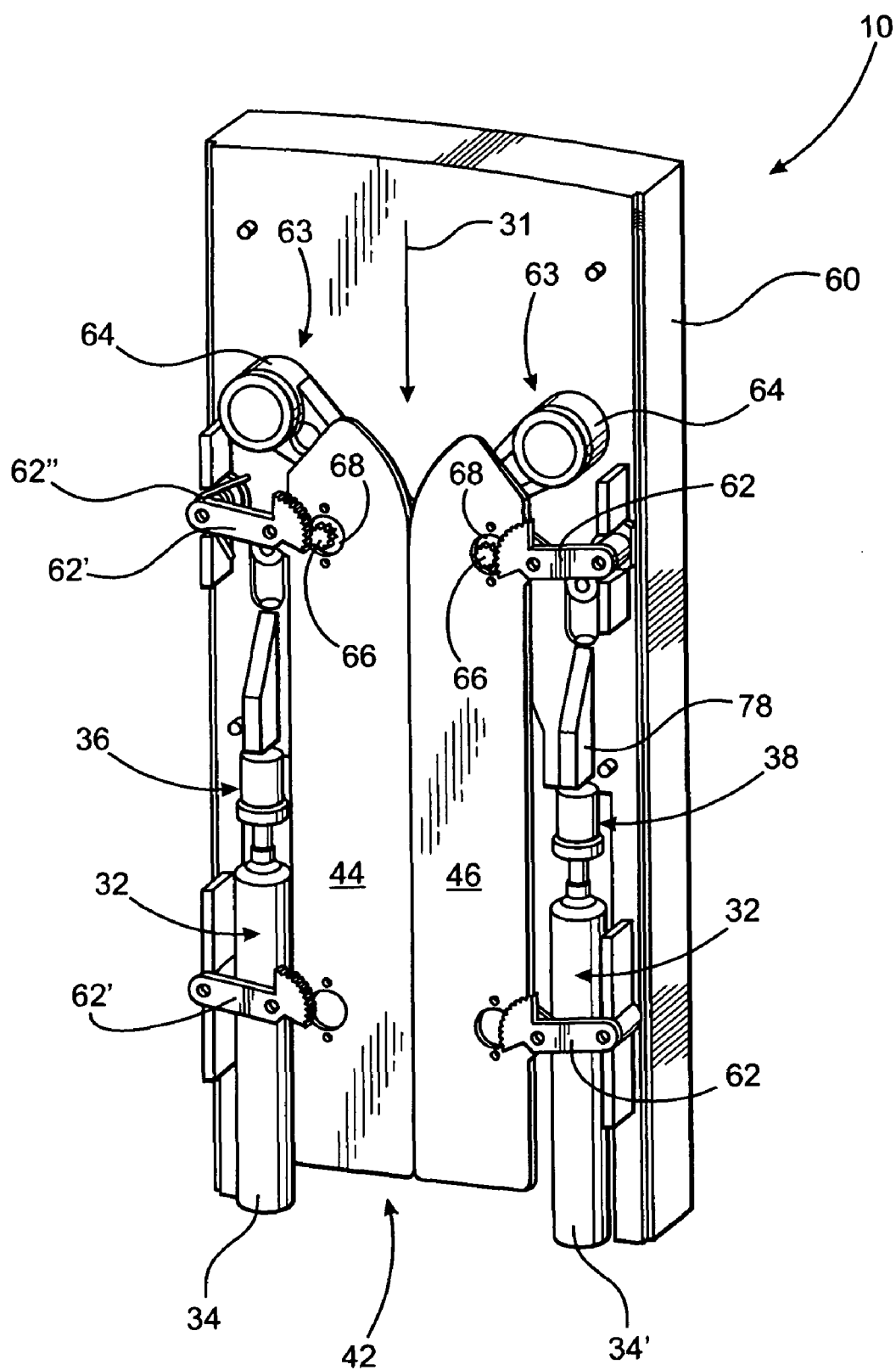
FIG. 3 is an interior perspective view of the embodiment of FIGS. 1 and 2 including a closure or gate assembly, which restricts unauthorized access to the interior of the cleaning assembly of the present invention and exposure of a user to cleaning fluid dispensed on the interior of the cleaning assembly.

In order to facilitate the prevention of the cleaning fluid from exiting through the open channel 30 of the housing 12, as well as prevent tampering or an unauthorized access to the interior of the housing or casing 12, the present invention includes a closure or gate assembly best represented in FIG. 3. More specifically, the closure or gate assembly is generally indicated as 42 and includes two gate members 44 and 46 normally disposed in a closed orientation as represented in FIG. 3. The gate members 44 and 46 are interconnected by connecting brackets or linkage 62, 62' interconnecting with attachment links 66 extending through aperture 68 in the gate member 44 and 46. The provision of a biasing spring 62", associated with at least one of the connecting links 62, serves to bias the gate members 44 and 46 in the closed, original position of FIG. 3. However, upon placement of the stethoscope head 14 through the entrance portion 24 of the casing 12 and by further movement of the head 14, using the aforementioned swiping action exerted thereon, the gate members 44 and 46 will be forcibly separated from one another into an open position. The open position comprises a separation of the gate members 44 and 46a sufficient distance to allow passage of the head 14 therebetween and along the length of the predetermined path of travel 30, 31.

Upon removal of the head 14 from the housing 12 through the exit portion 26, the gate members 44 and 46 will become disengaged from the head portion allowing them to assume the original, closed position of FIG. 3. This is due, at least in part, to the biasing force exerted thereon by the biasing spring 62". Also, when in the closed position of FIG. 3, any excessive spillage or over spray of the cleaning fluid will be prevented from exiting the casing 12 through the elongated channel 30, thereby segregating the user from such excess exposure to the cleaning fluid. As should be apparent, the disposition of the gate members 44 and 46 in the closed position of FIG. 3 will also restrict or lessen the possibility of tampering with the internal operative and structural components of the cleaning assembly 10. As such, the user will not be exposed spillage, over-spray or any excessive amounts of the cleaning fluid during or after the cleaning procedure.

With primary reference to FIG. 10, the aforementioned path of travel is also schematically and partially defined by directional arrow 31 which is intended to represent the direction of travel of the diaphragm 16 and other portions of the head 14 as it travels on the interior of the housing 12, along the path of travel 30 by virtue of the single, unidirectional, swiping action exerted on the head 14 by the user.

Figure 7:
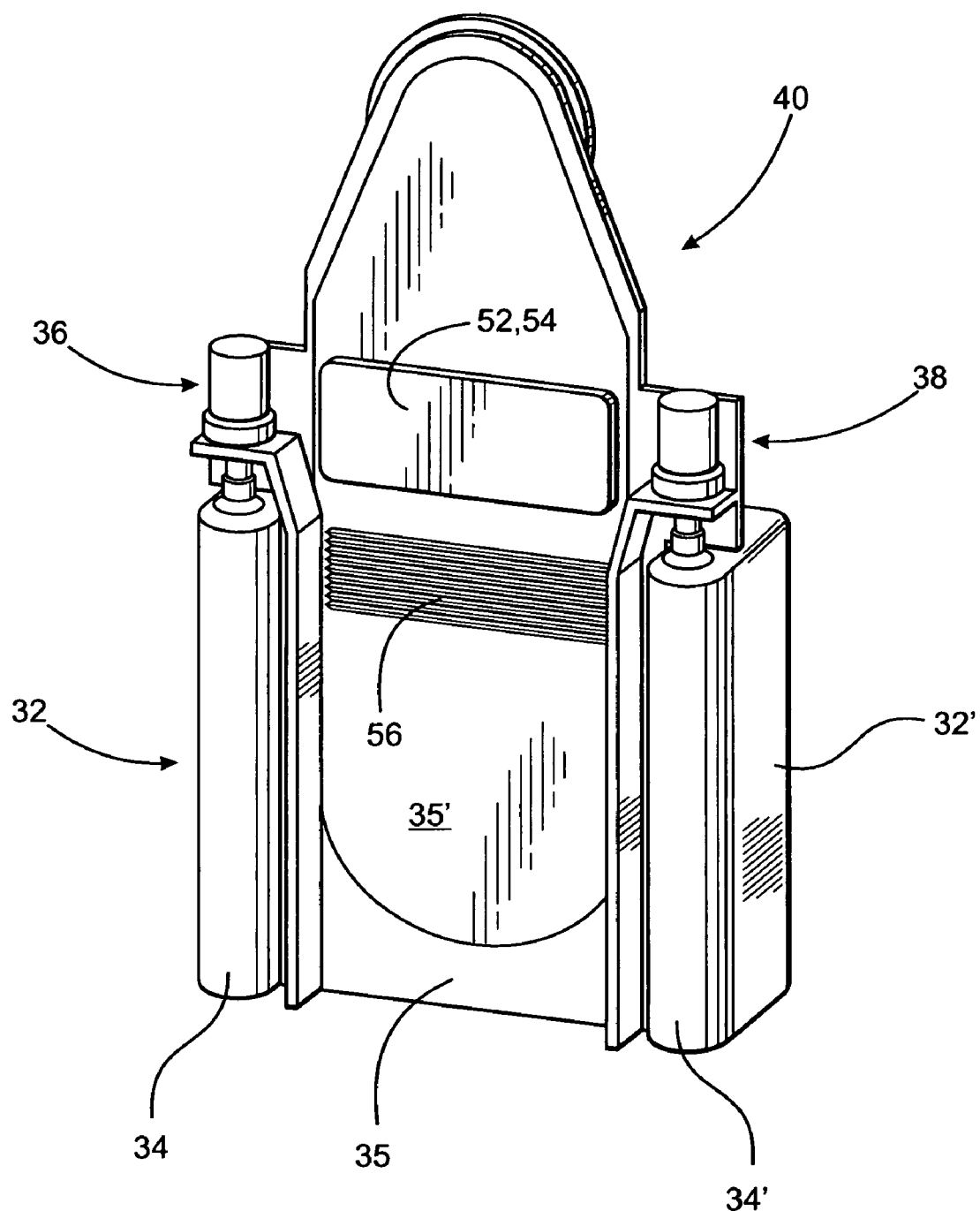
FIG. 7 is a perspective view of another preferred embodiment of the present invention directed to fluid supply assembly and applicator assembly structurally combined as part of a replaceable cartridge removably mounted within an interior of a housing of the cleaning assembly.
Figure 8:
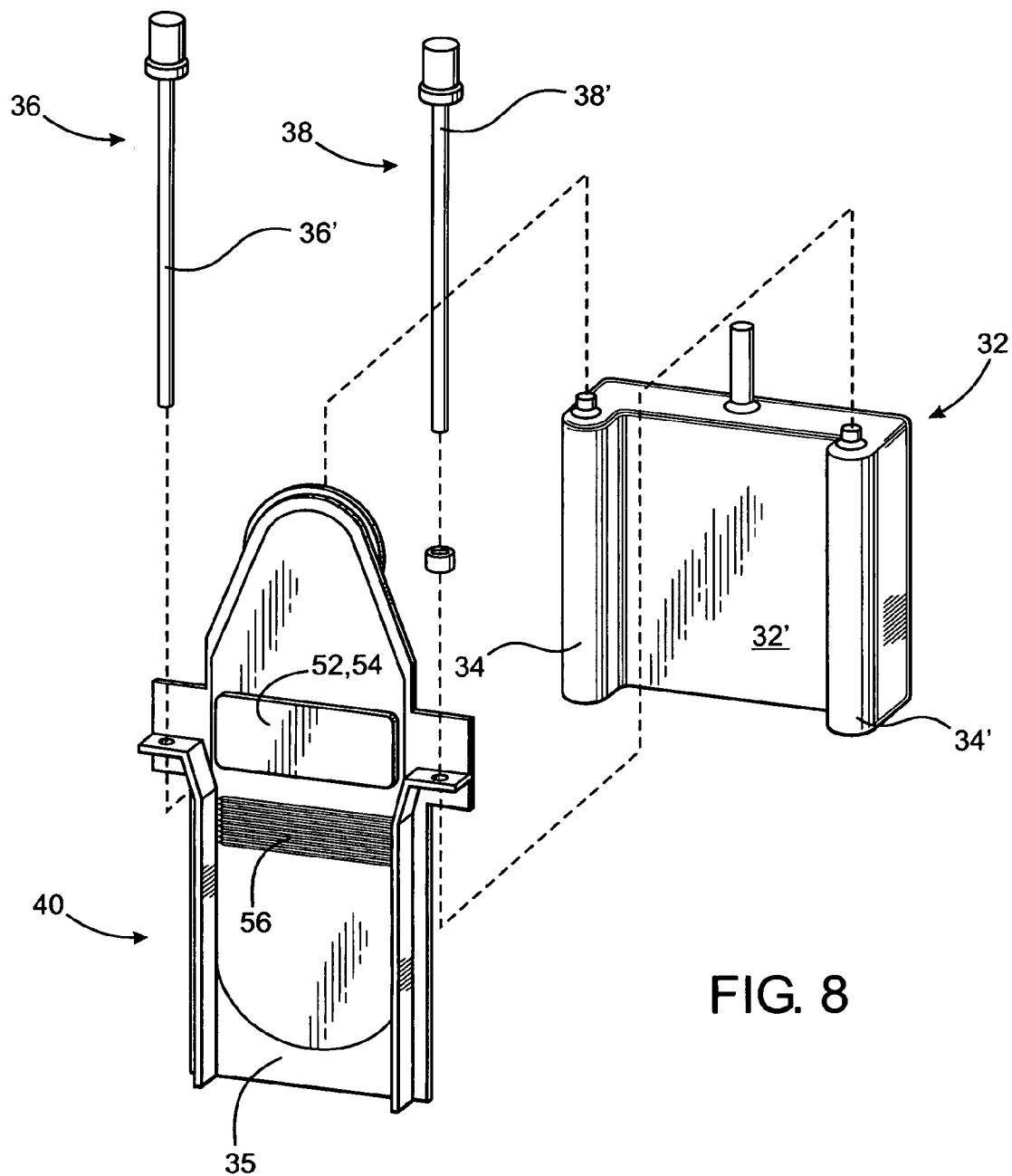
FIG. 8 is an exploded view of the embodiment of FIG. 7.
Figure 9:
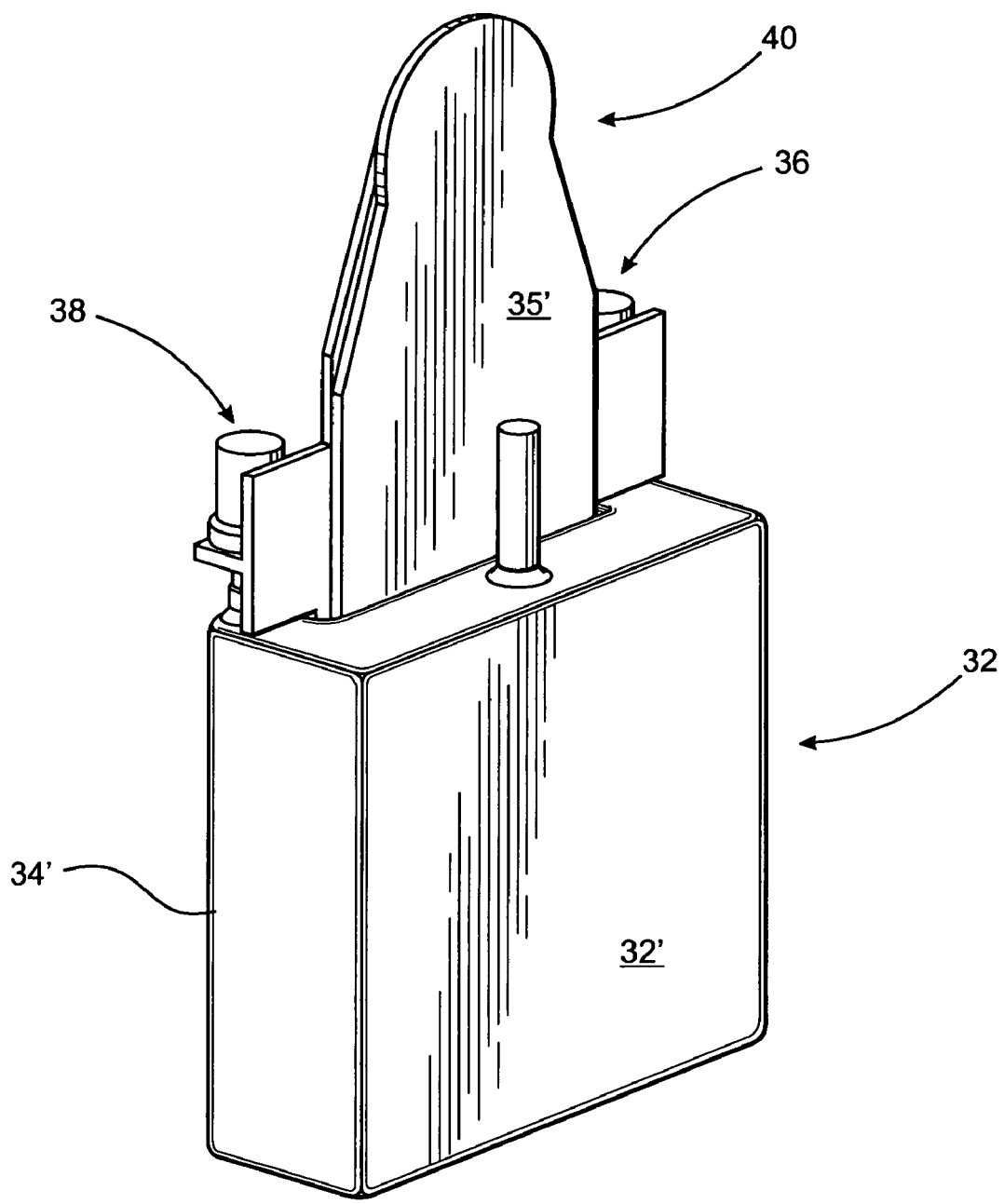
FIG. 9 is a rear perspective view of the embodiment of FIGS. 7 and 8.

Additional structural and operative features of the cleaning assembly 10 include a fluid supply generally indicated as 32 and more specifically comprising at least one, but possibly a plurality of fluid reservoirs 34 and 34'. Each of the fluid reservoirs 34 and 34', and accordingly the fluid supply 32, is structured to contain an appropriate quantity of cleaning fluid. As represented in FIGS. 7, 8, and 9 the fluid supply 32 may also include a fluid supply cartridge 32' having an access opening 33 to facilitate filling thereof. Moreover, the supply container 32' may be connected in fluid communication with the fluid reservoirs 34 and 34', so as to supply cleaning fluid thereto. As further represented the fluid supply assembly 32 and the structural and operative components associated therewith are removably mounted and/or connected to a supporting frame 35 on the interior of the casing 12, preferably as part of a replaceable cartridge 100. An alternative but additional preferred embodiment comprises each of the fluid reservoirs 34 and 34' containing an independent supply of cleaning fluid. Regardless of which embodiment of the cleaning fluid supply 32 is utilized, the composition of the cleaning fluid is preferably alcohol based and may comprise an antimicrobial liquid. The cleaning fluid is thereby formulated to effect a cleaning, disinfecting and/or sterilizing action on exposed portions of the head 14 while it passes in the intended direction 31 along the path of travel 30 on the interior of the housing 12.

Each of the reservoirs 34 and 34' are associated with a different dispenser assembly 36 and 38 preferably, but not exclusively, in the form of separate pump and/or dispensing valve mechanisms which include spray nozzles or heads 36" and 38". As also represented each of the dispenser assemblies 36 and 38, being in the form of pump mechanisms, may each include a dip tube 36' and 38' respectively, which are disposed within the interior of the corresponding reservoirs 34 and 34'. In a most preferred embodiment of the present invention each of the pump mechanisms 36 and 38 defining respective ones of dispenser assemblies are operative when a downward or other appropriately directed force is exerted thereon. The applied force is of sufficient magnitude to cause the dispensing of the cleaning fluid from within the respective fluid reservoirs 34 and 34' onto at least a portion of an applicator assembly 40, to be described in greater detail with specific reference to FIG. 7 through 10.

Dispensing of the cleaning fluid is accomplished by operative interaction of the fluid supply assembly 32 and more specifically, the dispenser assemblies 36 and 38 with an activating assembly generally indicated as 63. The activating assembly 63 includes at least one but preferably a plurality of activating members 64 preferably in the form of lever arms and which are equal in number to the one or more fluid reservoirs 34 and 34' and associated dispenser assemblies 36 and 38. As should be apparent, each of the one or more activating members 64 are movably connected on the interior of the housing 12 and are normally biased or otherwise positioned into an initial position represented in FIG. 4. However, the connection and structure of each of the activating members 64 is such as to facilitate cooperative disposition of the activating members 64 into an operative position represented in FIG. 5.

Figure 4:
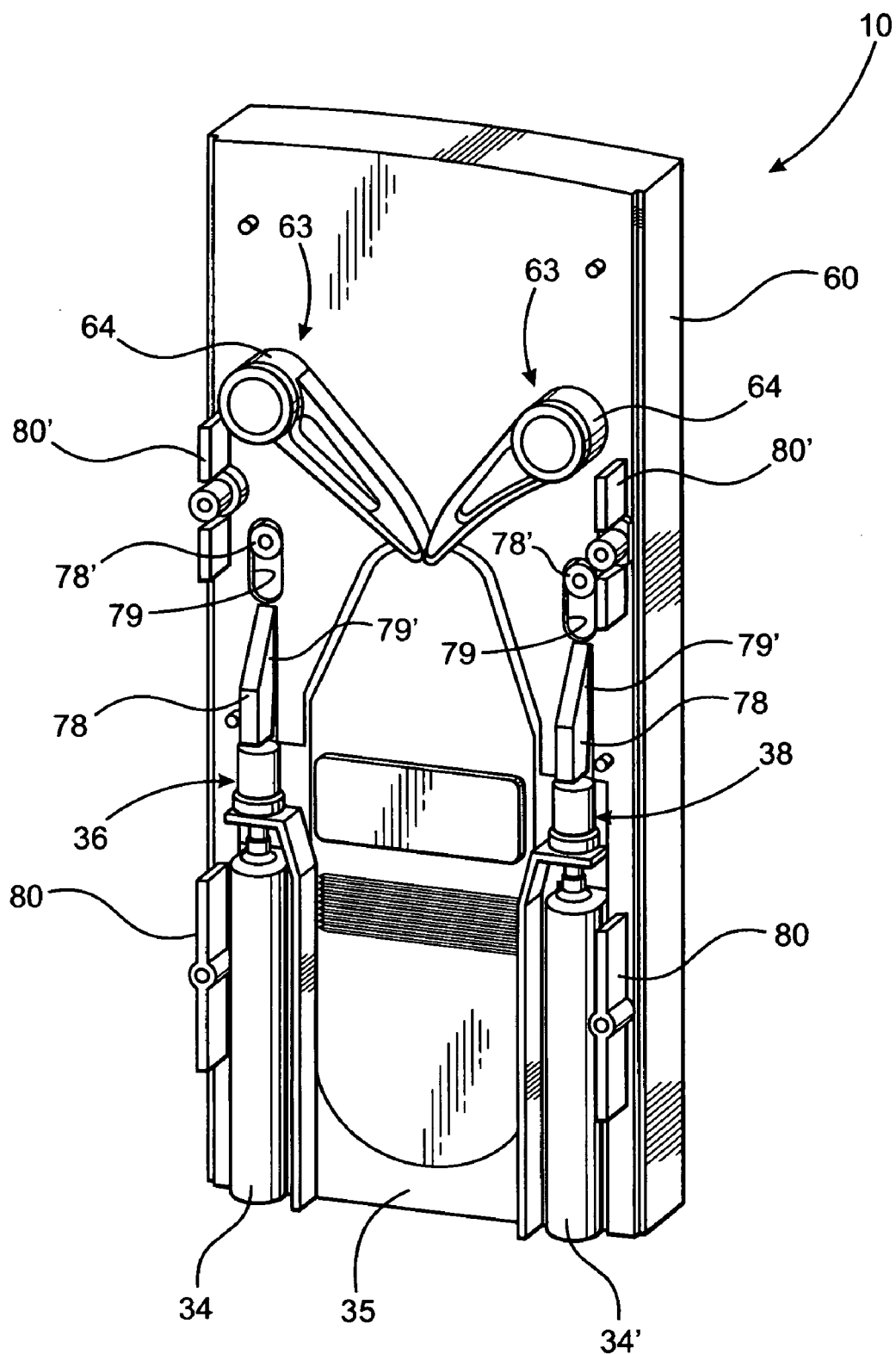
FIG. 4 is an interior perspective view of various operative components of the present invention in an initial position.

With primary reference to FIG. 4, the initial position of the activating members 64 are such as to be disposed in substantially interruptive relation to the path of travel 30 and more specifically, in interruptive relation to the head 14 passing in the intended direction 31 along the path of travel 30. Accordingly, once the head 14 passes into the entrance 24 and begins to travel along the aforementioned path of travel 30, portions of the head 14 located on the interior of the casing 12 will engage each of the activating members 64 in driving relation thereto forcing the activating members 64 into an operative position represented in FIG. 5. As such, a substantial "camming" action will occur between the forced travel of the head 14 and the engaged portions of the activating members 64. Such driven engagement will force the activating members 64 into the operative position of FIG. 5 and into operative, activating position and/or relation to the respective dispenser assemblies 36 and 38.

Such operative engagement between the activating members 64 and the dispenser assemblies 36 and 38 involves an appropriately directed driving and/or operating force being applied to the respective dispenser assemblies 36 and 38 and accordingly the pump mechanisms defined thereby. An appropriate mechanical linkage assembly, collectively represented in FIGS. 3 through 6, 11 and 12, is disposed and structured to operatively interconnect each of the activating members 64 with corresponding ones of the dispenser assemblies 36 and 38 respectively.

As represented the mechanical linkage assembly may assume a variety of structural and operative features which serve to transfer a sufficient driving or activating force from the activating members 64 to the dispenser assemblies or pump mechanisms 36 and 38. Such a driving, activating force will be established by the activating members 64 being forcibly driven by their engagement with the head 14 as it passes along the path of travel 30 in the intended direction 31. Accordingly, the operative position of the activating assembly 63 and more specifically, the activating members 64 may be further defined by their driven engagement with the head portion 14 and their concurrent driving, operative relation to each of the dispenser assemblies 36 and 38, due to the provision of the aforementioned and represented linkage assembly, as the head portion 14 passes along the path of travel 30.

With primary reference to FIGS. 4-6, 11 and 12, operative features of the cleaning assembly 10 of the present invention are more clearly represented by a more detailed description of the structural and operative components primarily, but not exclusively, associated with the linkage assembly. In addition, the operative inter-workings of the various components associated with the mechanical linkage assembly will better facilitate an understanding of the cooperative structuring and operation of the activating assembly 63. This will be demonstrated in terms of the activating members 64 engaging and being driven by the head 14 into the operative position generally indicated in FIG. 5, as the head 14 travels along the intended path of travel 30 in the intended direction 31. Accordingly, a mounting frame 60 is connected on the interior of the casing 12 and is structured to at least partially and preferably removably support and cooperatively position the fluid supply assembly 32 and the activating assembly 63. As will be apparent the intended cooperative positioning of the fluid supply 32 and the activating assembly 63 is such as to force a dispensing of the cleaning fluid from each of the reservoirs 34 and 34' by means of appropriate forces being exerted on the respective dispenser assemblies 36 and 38 which, as set forth above, may be in the form of pump mechanisms. As represented throughout the accompanying Figures, each of the one or more pump or dispensing valve mechanisms defining the dispenser assemblies 36 and 38 also include a spray head or nozzle 36" and 38"

Figure 11:
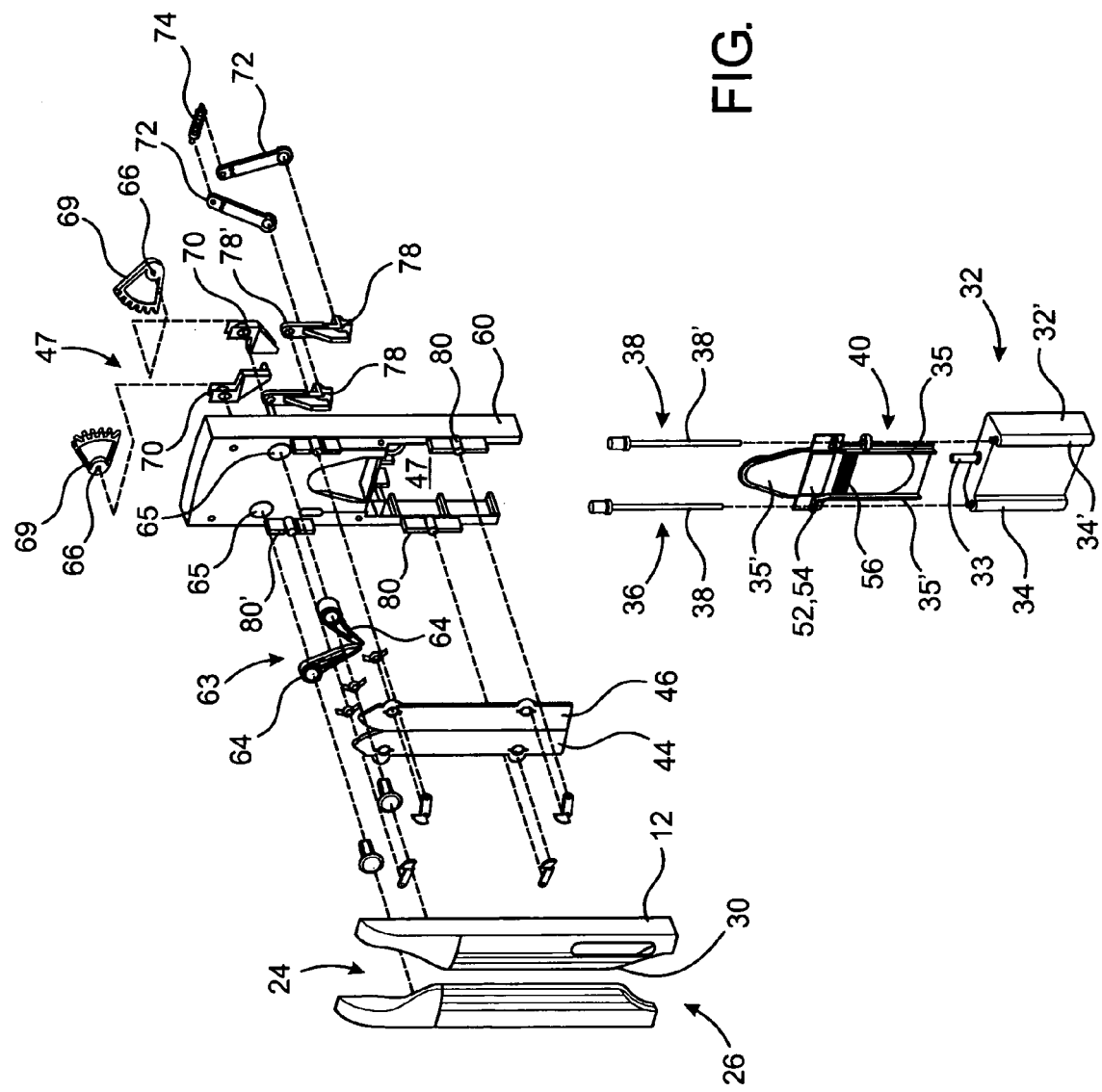
FIG. 11 is a front perspective view in exploded form of a plurality of the operative components collectively comprising at least a portion of a linkage assembly serving to operatively interconnect the activating assembly to a fluid supply assembly for the dispensing of cleaning fluid onto the head of the stethoscope being cleaned.
Figure 12:
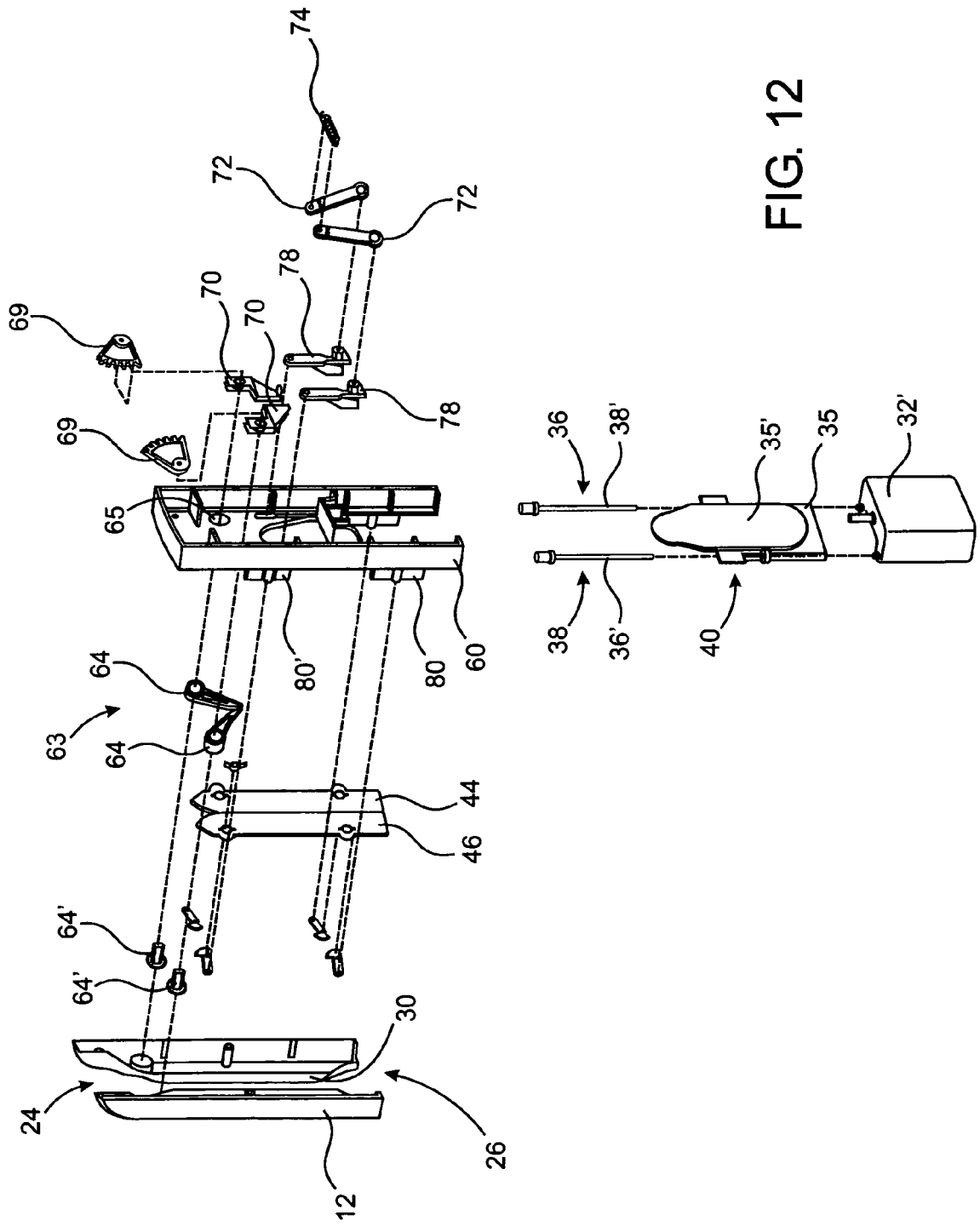
FIG. 12 is a rear perspective view in exploded form of the operative components associated with the embodiments of FIG. 11.

As represented in FIGS. 11 and 12, each of the activating members or lever arms 64 pass through appropriate apertures 65 in the mounting plate 60. Moreover, the lever arms 64 communicate with the additional mechanical linkage, represented in FIG. 6, located on the opposite or rear side of the mounting frame 60. Accordingly, passage of the head 14 along the path of travel 30, 31 will cause an outward pivotal movement or separation of the first lever arms 64 from the initial position of FIG. 5 to the operative position of FIG. 6.

Figure 5:
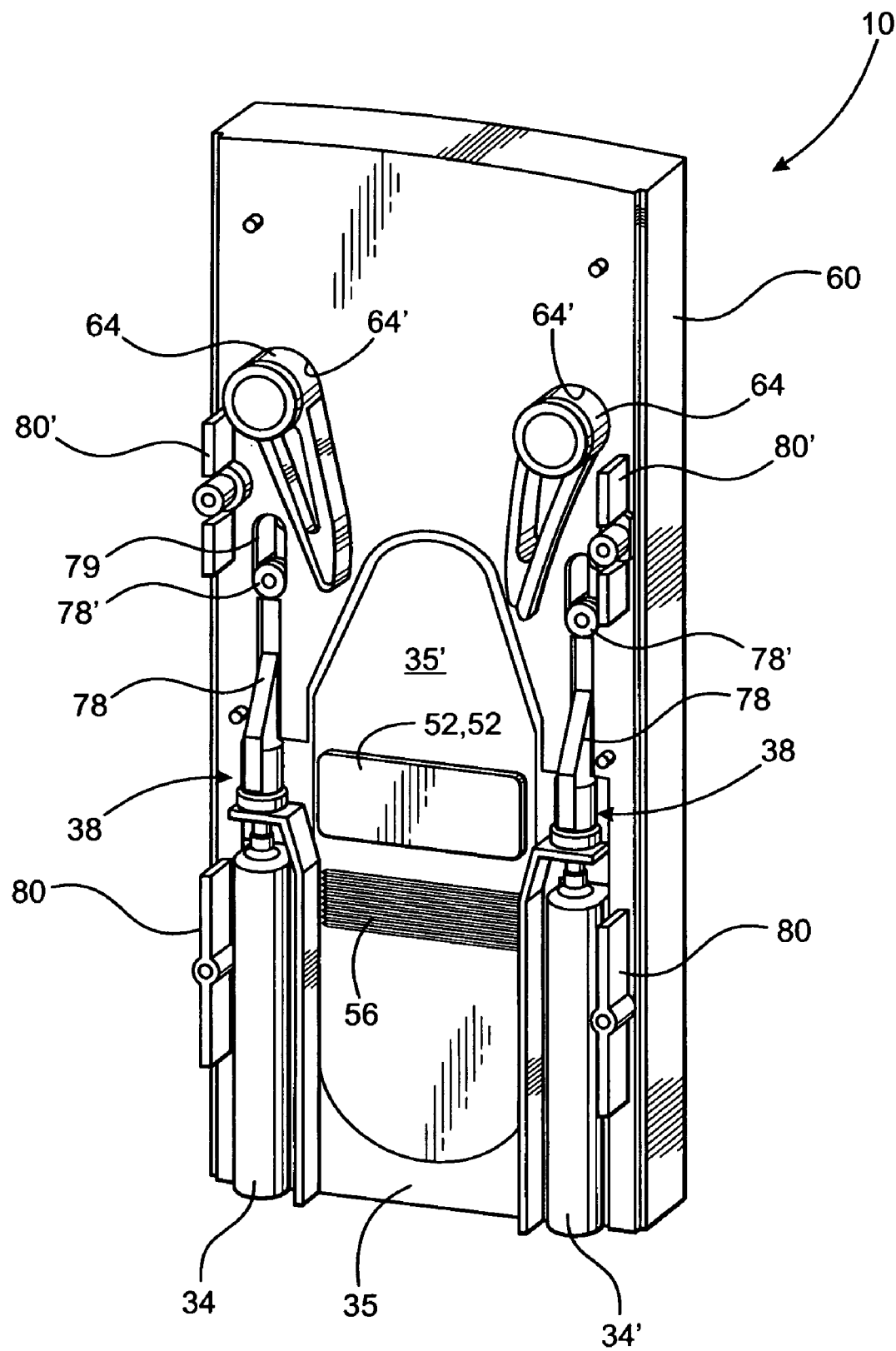
FIG. 5 is an interior perspective view of the present invention wherein certain components are in an operative or activated position for dispensing of cleaning fluid.
Figure 6:
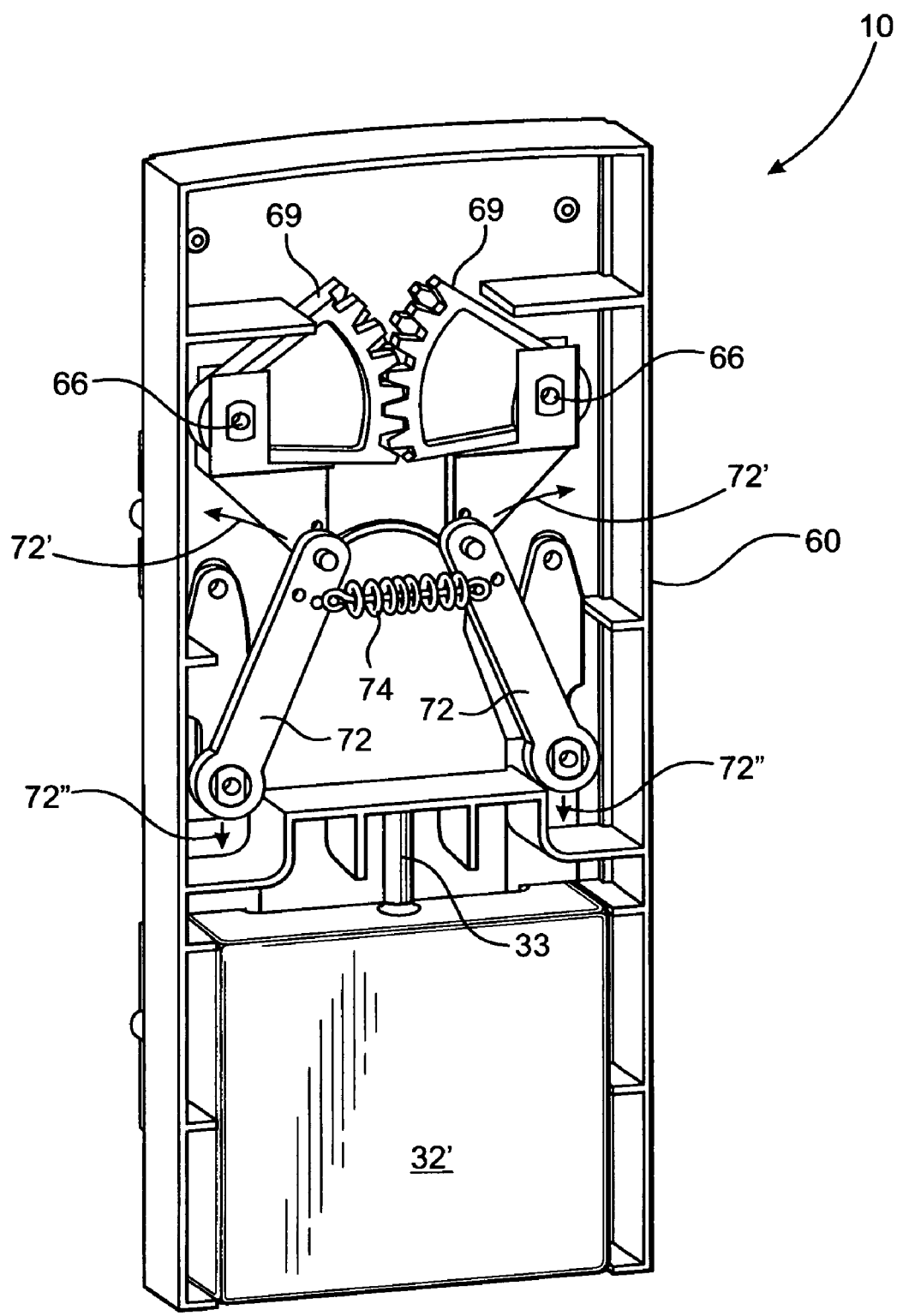
FIG. 6 is a rear perspective view of the embodiments of FIGS. 4 and 5.

As represented in FIGS. 4 through 6, the lever arms 64 are also connected to individual gear segments 69 on the opposite side of the mounting frame 60 relative to the actuating members, lever arms 64. As such each gear segment is movable with a corresponding one of the lever arms 64 as they pass from the initial position of FIG. 5 to the operative position of FIG. 6. Of course, it recognized that the term gear segment 69 can refer to an actual gear or other mechanism which achieves the desired movement. As also shown in FIG. 6, each of the gear segments 69 are disposed in meshed engagement with one another and are attached to separate connecting links 70. In turn, each connecting link 70 is movably connected and drivingly attached to corresponding ones of a second set of lever arms 72. The lever arms 72 are connected in a biased relation to one another by a biasing spring 74 and are thereby normally maintained in the initial position as that of the first set of lever arms 64 as represented in FIG. 4.

Accordingly, a separation or appropriate relative movement of the activating members, lever arms 64 as they engage the head 14 passing along the path of travel 30, in the intended direction 31, will cause an outwardly directed movement of the lever arms 72 in accordance with directional arrows 72' as well as a substantially downward movement of the lower end of the secondary lever arms 72 as indicated by directional arrows 72".

As best represented in FIGS. 4 through 6, the lower ends of each of the lever arms 72 are connected to plunger members 78. Accordingly, as the lower ends of the lever arms 72 pass downwardly or in another appropriate direction 72" they will forcibly engage and drive the plunger members 78. This will force each of the plunger members 78 to engage and apply an activating force to corresponding ones of the dispenser members 36 and 38, causing a dispensing of the cleaning fluid. Appropriate channels or elongated slots as at 79 and 79' are provided of sufficient dimension and configuration to facilitate the downward passage or other appropriately directed travel of both the plunger members 78 and interconnected plunger heads 78' associated therewith.

Therefore, as set forth above and explained with the schematic representation of FIGS. 4 through 6 and 10, a single, unidirectional, one handed, "swiping" passage of the stethoscope head 14 into the entrance 24 and along the path of travel 30 will cause the separation of the activating members 64. Accordingly, the forced separation of the activating members 64 will in turn deliver an activating force to the dispenser members 36 and 38. This activating force will cause cleaning fluid to be delivered to an applicator assembly 40 as represented in FIG. 7 through 10 and described in detail hereinafter.

With primary reference to FIG. 10, one preferred embodiment of the aforementioned applicator assembly 40 includes a plurality of applicator members 52, 54 and 56. It is emphasized that the intended spirit and scope of the present invention may include a greater or lesser number of applicator members and their disposition within the casing 12 may vary from that represented in FIG. 4. However, regardless of the various possible structural and operative modifications, the applicator assembly 40 is disposed and structured to apply the cleaning fluid to the intended, exposed portions of the head 14. In addition in the embodiment of FIG. 10a cleaning engagement and a finishing engagement is also preferably included to complete the cleaning procedure. More specifically, applicator member 52 comprises an at least partially absorbent or non-absorbent applicator material as at 52' disposed in receiving relation to cleaning fluid being dispensed from the one or more fluid reservoirs 34 and 34'. Accordingly, the dispenser assemblies or pump mechanisms 36 and 38 are disposed and structured to dispense fluid directly onto the applicator member material 52'. As the head 14 travels along the path of travel 30, 31 it will engage and apply the cleaning fluid directly to the exposed, intended surfaces or portions of the cleaning head 14. It should be further noted that the dispenser assemblies 36 and 38 may include structural orientation features associated therewith, such that the cleaning fluid will be consistently dispensed on to an appropriate portion, as at 52, 52' of the applicator assembly 40 to assure proper cleaning of the head 14.

While at least one preferred embodiment of the present invention comprises the cleaning fluid delivered to the applicator member 52, it is also contemplated that the cleaning fluid could be applied directly onto the surface(s) of the head 14 which are to be cleaned, rather than on the applicator member. In such a modification, the applicator member 52 would still be disposed and structured to perform the desired distributing, wiping or other appropriate action on the surfaces of the head 14 in order to facilitate the cleaning thereof.

Further with regard to the structure and function of the applicator assembly 40, as the head 14 continues to travel along the path of travel 30, in the intended direction 31 on the interior of the housing 12, it will preferably engage a cleaning member 54' mounted on or otherwise directly associated with the applicator member 54. In at least one preferred embodiment of the present invention, the cleaning member 54' is defined by a brush and/or bristle array or assembly and/or contact elements. As such, the cleaning fluid existing on the intended portions of the head 14 will be spread over and thoroughly engage all intended portions of the cleaning head 14, including the diaphragm 16 and/or other contiguous surface portions. Further, the structuring of the brush or bristle array or assembly 54' may be such as to provide an at least mildly abrasive engagement or action so as to accomplish thorough cleaning, disinfecting, sterilizing, etc. Naturally, materials other than a brush 54' may be utilized and the cleaning engagement applied to the diaphragm 16 and other portions of the head 14 may be other than mildly abrasive.

As the cleaning head 14 continues to travel in the intended direction 31 along the path of travel 30, it will engage a finishing structure 56' mounted on or directly associated with the applicator member 56. In at least one preferred embodiment, the finishing member 56' comprises one or a plurality of "squeegee" members which engage exposed portions of the head 14 and as such serve to remove excess cleaning fluid still remaining thereon. The head 14 will thereby be dried or at least partially dried. Subsequent to passage beyond the applicator member 56, the head 14 is removed from the interior of the housing 12 through the exit portion 26.

Accordingly, the squeegee assembly may include one or more ribs which may be flexible or otherwise appropriately structured to movably engage the exposed diaphragm and/or rib surface of the head 14 so as to remove excess cleaning fluid there from. Further, the squeegee assembly is located on the interior of the housing 12 and as such will direct, deposit or otherwise facilitate collection of the removed, excess cleaning fluid on the interior of the housing 12 for eventual removal, as indicated.

It is emphasized that while the structures and materials of the one or more applicator members 52, 52'; 54, 54' and/or 56, 56' may be disposed and structured to provide a different type of cleaning engagement with the surfaces or parts of the head portion intended to be cleaned, all of the different types of cleaning procedures may be accurately and generically described herein as performing a "cleaning action".

As set forth above, the applicator assembly 40 can include a plurality of applicator members which may vary in position, number and purpose. By way of example, the embodiment of FIGS. 4-8 and 11 may differ from the embodiment of FIG. 10 by including an applicator assembly 40 preferably comprising two applicator members including a combined absorbent applicator member 52 and/or cleaning brush type structure or array 54. Accordingly, it is intended that one or more of the various members 52, 54, 56, etc. may be combined in function and structure, at least to the extent of effectively and efficiently cleaning the intended and exposed portions of the cleaning head 14 as it passes along the intended path of travel 30, 31.

As also clearly represented in FIGS. 7 through 9, 11 and 12, the fluid supply assembly 32 along with the individual fluid dispensers 36 and 38 may be effectively combined to define a removable, replaceable cartridge assembly collectively indicated as 100. Moreover, one or more of the cartridge assemblies 100 may be removed, replaced, repaired, refilled, etc. and as such are securely but removably connected to the carrier frame 60. As such, a mounting panel 35' may be structured to support and/or have secured thereon the plurality of applicator members 52, 54, 56, etc. and be fixedly or removably connected to the base 35. Also, the base 35 of the supporting panel 35' may be interconnected to the fluid supply assembly 32, including the supply container 32', wherein the separate reservoirs 34 and 34' are also operatively connected to container 32'. Accordingly, the assembled cartridge 100, as represented in FIGS. 6-8, comprises the combined fluid supply assembly 32 and applicator assembly 40 and may be removably connected to the carrier frame 60, as best represented in FIGS. 11 and 12. Removable attachment of the cartridge 100 may be accomplished by connectors 80 by other appropriate means. As such, the bracket like connectors 80 may be used to facilitate the attachment of other operative components of the cleaning assembly 10 including the various individual linkage components also represented in FIGS. 11 and 12.

Accordingly, it should be apparent that effective and reliable cleaning of exposed portions of the head 14 can be accomplished by a single, unidirectional, "swipe" of the cleaning head 14 along the path of travel 30. Therefore, repeatedly passing or like reciprocally directed movement or travel of the cleaning head 14 is not required. As such, many of the disadvantages and problems recognized in conventional or known cleaning devices intended for this purpose are overcome.

Additional structural features of the present invention are represented in FIGS. 1 and 2 and comprise an indicator assembly generally indicated as 90. The indicator assembly may include a plurality of related and operatively appropriate components including a viewing structure such as window 92 cooperatively disposed on the housing and/or on the one or more reservoirs 34 and 34' and/or the fluid supply container 32'. As such, the quantity of cleaning fluid remaining therein may be visually observed. A user can determine when additional cleaning fluid need be replaced in the one or more reservoirs 34 and/or 34' and/or the fluid supply container 32'. In addition, the indicator assembly 90 may or may not include a float structure 94 which may have an appropriate specific gravity to allow it to float on the top of the liquid level of the cleaning fluid. As such movement of the float structure 94 will correspond to the level of cleaning fluid remaining in one or both of the reservoirs 34 and/or 34' and/or the fluid supply container 32'. The embodiments of FIGS. 1 and 2 represent the indicator assembly 90 including a single viewing structure or window 92 as well as a single float structure 94. However, the intended spirit and scope of the present invention includes the indicator assembly 90 also comprising a plurality of such windows or viewing structures 92 and/or a plurality of float structures 94. In either of these embodiments, the viewing structures or windows 92, provided with or without the float structures 94, are appropriately and operatively positioned relative to one or more of the reservoirs 34 and 34' and/or the fluid cartridge 32' so as to determine the remaining quantity of cleaning fluid in the cleaning assembly 10.

Figure 13:
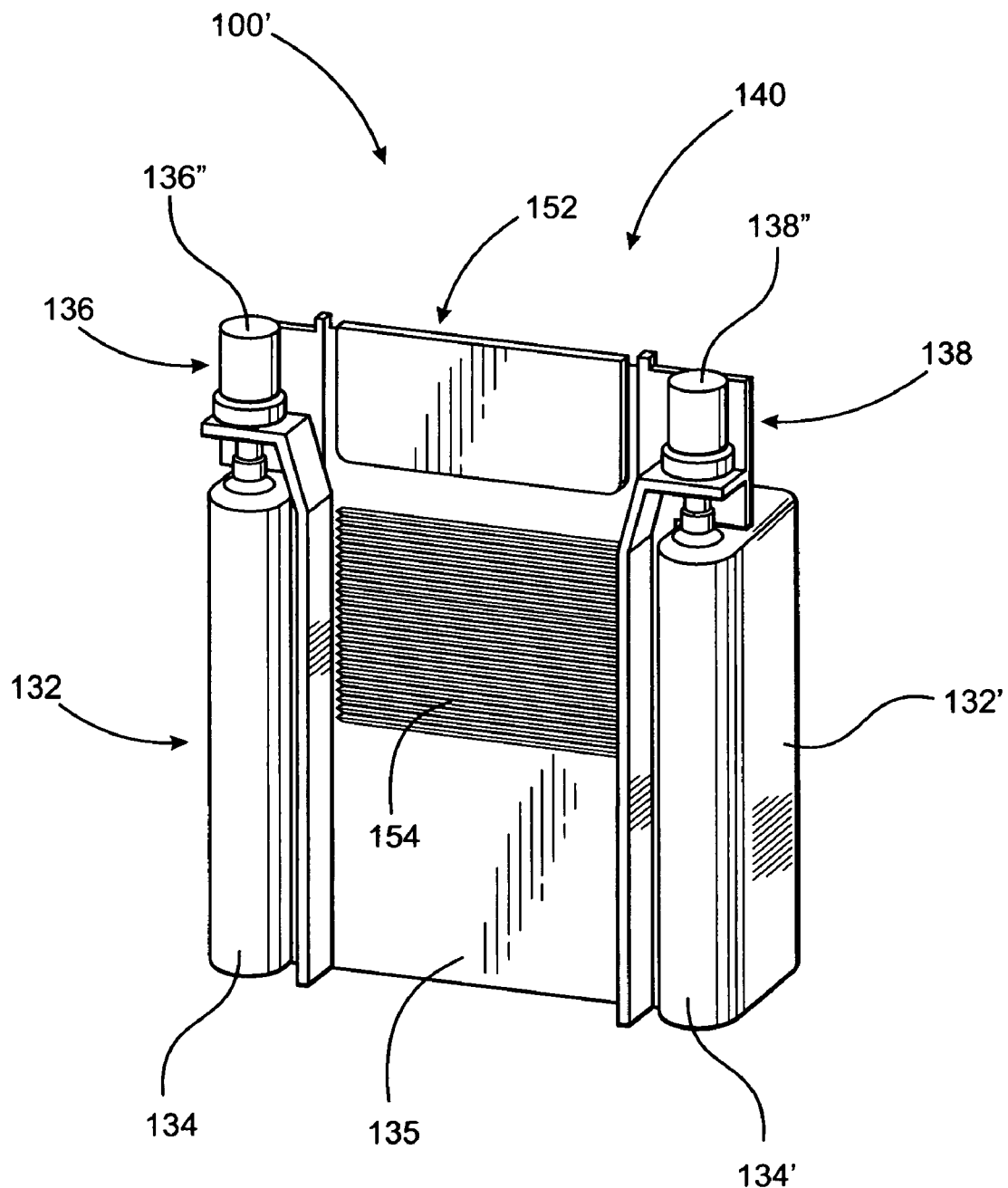
FIG. 13 is a front perspective view of yet another preferred embodiment of a replaceable cartridge assembly structured to be removably mounted within the housing of the cleaning assembly.
Figure 14:
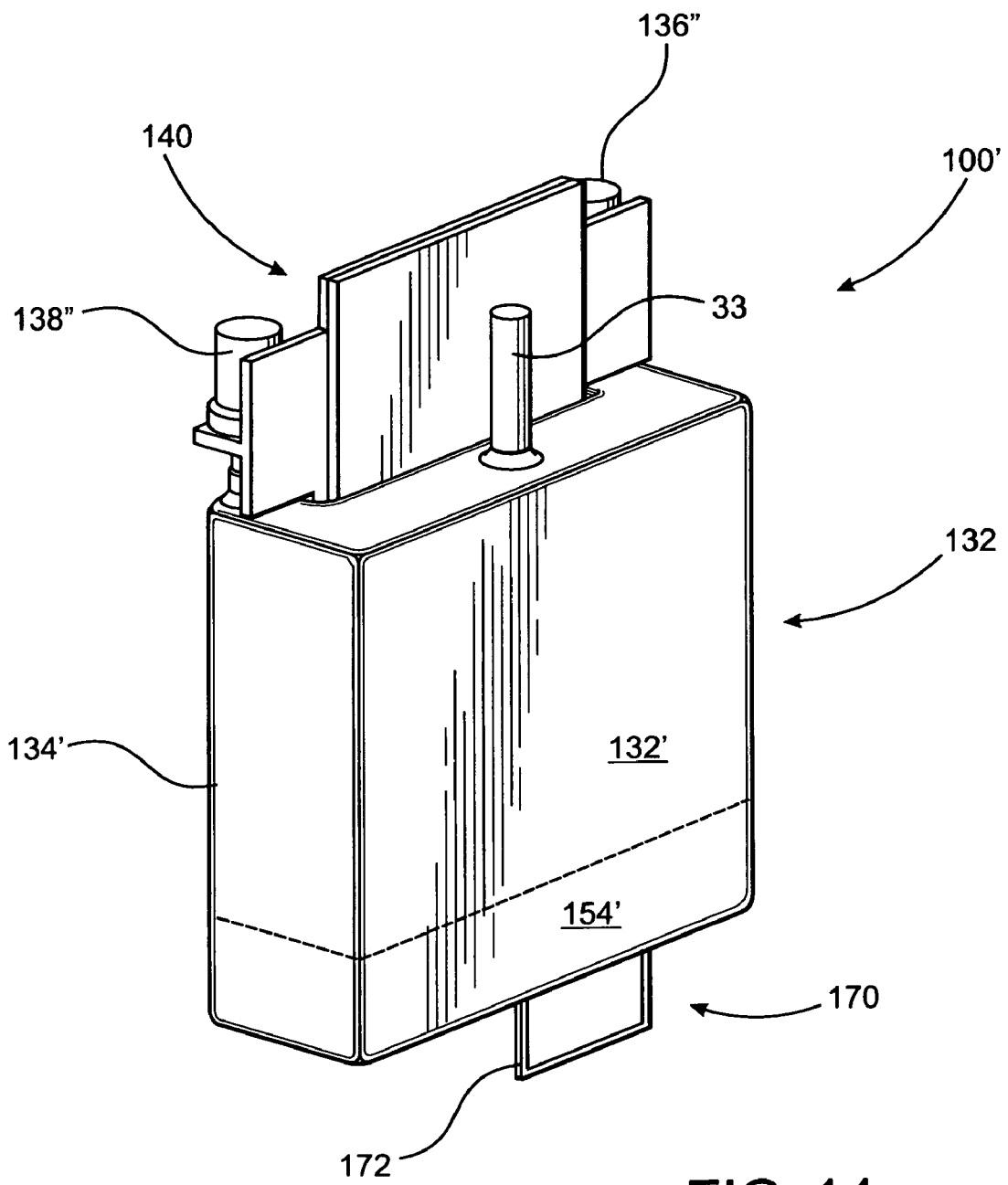
FIG. 14 is a rear perspective view of the embodiment of FIG. 13.

Yet another preferred embodiment of the present invention is directed to a removable, replaceable cartridge 100' as represented in FIGS. 13 and 14. The replaceable cartridge 100' is operatively similar but at least somewhat structurally distinguishable from the removable cartridge 100 as represented in FIGS. 7 through 9. Also, cartridge 100' includes many of the structural and operative features, set forth in detail above, with reference to the cartridge 100, including, but not limited to, a fluid supply assembly 132 and an applicator assembly 140. In addition, the activating assembly 63, including at least one but preferably a plurality of activating members 64, is operatively associated with the dispenser assemblies 136 and 138 also in the manner described in detail above and represented throughout the Figures.

Yet additional structural features of the removable, replaceable cartridge 100' includes the fluid supply assembly 132 comprising at least one but preferably two fluid reservoirs 134 and 134' structured for containing cleaning fluid which is dispersed through interaction between the activating assembly 63, as set forth above, and the dispenser assemblies 136 and 138. As with the previously described cartridge 100, each of the dispenser assemblies 136 and 138 include a dispensing head or nozzle 136" and 138" as well as associated dip tubes or other dispensing components not specifically represented in FIGS. 13 and 14. The removable cartridge 100' further includes a fluid container 132' which may hold an appropriate amount of cleaning fluid. The cleaning fluid contained within the fluid container 132' may be transferred or otherwise disposed in fluid communicating with the individual reservoirs 134 and 134' or be independently stored therefrom.

As also represented in FIGS. 13 and 14, the removable, replaceable cartridge 100' includes the aforementioned applicator assembly 140. The applicator assembly 140 comprises at least one but preferably a plurality of applicator members 152, 154, etc. disposed adjacent to one another along the supporting frame or base 135. It is emphasized that while the applicator members 152 and 154 are represented in spaced relation to one another on the supporting frame or base 135 they may also be disposed in substantially contiguous relation to one another, such that the ending of the applicator member 152 is contiguous to the beginning of the applicator member 154. Further, the materials from which the applicator members 152, 154, etc. are formed may differ so as to provide different "cleaning actions" when the applicator members confrontingly engage the surfaces of the head portion intended to be clean.

As described with specific reference to the embodiment of FIG. 10, the materials from which the applicator members 152, 154, etc. are formed may provide different types of cleaning actions such as, but not limited to, wiping, finishing, cleaning or providing a mild abrasive action, etc. Further by way of example, applicator member 152 may comprise an at least partially absorbent or non-absorbent applicator material disposed in receiving relation to cleaning fluid being dispensed from the one or more fluid reservoirs 134 and 134'. As such, the dispenser assemblies 136 and 138 and specifically the spray heads or nozzles 136" and 138" are disposed and structured to dispose fluid directly on to the upper most applicator member 152. The additional one or more applicator members 154, etc. are disposed somewhat beneath the upper most applicator member 152 and as such may receive, through gravity flow, the cleaning fluid dispensed onto the upper most applicator member 152. In order to accomplish such preferred directional dispensing of the cleaning fluid, it should be noted that in the embodiment of FIGS. 13 and 14, as well as the embodiment of the cartridge 100 as represented in FIGS. 7 through 9, the dispenser assemblies 136 and 138 are located somewhat "forward" of the applicator assembly 140. This disposition, along with a predetermined spray pattern issuing from the spray heads or nozzles 136" and 138" serves to preferably direct the cleaning fluid onto the upper most one of the applicator members 152. Thereafter, gravity flow of the cleaning fluid, as well as the travel of the head portion itself, will serve to at least partially transfer some of the cleaning fluid onto the other one or more applicator members 154, etc. However, structural modifications or other embodiments of the cartridge assemblies 100, 100' may also include the cleaning fluid being applied directly to the intended exposed surfaces of the head portion or alternately to additional ones of the applicator members 152, 154, etc. As also explained with regard to the embodiment of FIG. 10, as the head 14 continues to travel along the path of travel 30 in the intended direction 31 on the interior of the housing 12, it will preferably engage each of the plurality of applicator members 152, 154, etc.

In addition, the applicator assemblies 40 and 140, specifically including the respective applicator members associated therewith, may also include an appropriate cleaning agent, preferably in the form of an antimicrobial agent, incorporated and/or integrated directly in at least one or all of the plurality of applicator members. Moreover, the incorporation of such an antimicrobial agent directly into the materials of the plurality of applicator members would further enhance the cleaning of the head portion coming into contact therewith. More specifically, the structure of one or all of the applicator members is such that the antimicrobial agent integrated or incorporated therein will be applied to the engaged surfaces or portions of the head as it travels along the path of travel. Of course this will be in addition to the cleaning fluid directed on to the applicator member(s) through the spray heads or nozzles from the respective reservoirs. Also, such integration or incorporation of an appropriate antimicrobial agent will have the additional feature of preventing or significantly reducing the ability of microorganisms to colonize on the applicator members or other directly associated parts of the applicator assembly 40 and/or 140.

Further, in order to effectively assure that all of the intended surfaces of the head portion 14 are cleaned, at least one, but preferably all, of the applicator members 152, 154, etc. are formed of a malleable material. More specifically, the malleable material from which one or more of the applicator members 152, 154, etc. are formed has sufficient flexibility or other "conforming capabilities" to engage and thereby provide an appropriate cleaning action thereto. As noted herein, a typical structure of a head portion 14 of a stethoscope may include the centrally disposed diaphragm 16 and the surrounding of retaining rim 18. Accordingly, the malleable material from which one or more of the applicator members 152, 154, etc. are at least partially formed includes sufficient physical characteristics to assure conformance of the respective applicator members 152, 154, etc. to all of the exposed surfaces of the head portion 14 which are intended to be cleaned.

Additional structural features of the preferred embodiment of the cartridge assembly 100' may also include an indicator assembly generally indicated as 90 and specifically represented in the embodiments of FIGS. 1 and 2. The indicator assembly 90 may include a plurality of related and operatively appropriate components including a viewing structure, such as a window 92 cooperatively disposed on the housing or other viewable portions of the cartridge assembly 100' so as to view the interior content of the reservoirs 134 and 134' and/or the fluid container 132'. As a result, quantity determination of cleaning fluid remaining therein may be established. This will further facilitate a determination as to when the cartridge 100 or 100' need be removed from the housing 12 and replaced by a different "full" cartridge. Naturally, the cartridge 100 and 100' may be replaced for other reasons such as replacement or repair of the applicator members associated with the applicator assembly 40 or 140 and/or a malfunction of the dispenser assemblies associated with the removable, replaceable cartridge assemblies 100 and 100'.

In addition, in order to assure that the cartridge 100 or 100' is properly but removably disposed in its intended operative position within the housing 12, an appropriate locking assembly may be disposed on or within the housing and structured to securely but removably connect the cartridge(s) 100 or 100' in the aforementioned operative position. Further, such a locking assembly could be structured to produce a "click" or other appropriate sound indicating that the cartridge 100 or 100' is properly connected.

With primary reference to FIG. 14, additional structural features of the cartridge 100' may include a "disinfecting station" comprising a hand, automatic, or manually activated dispensing assembly 150. As a part thereof, a dispensing element 152 is disposed and structured to dispense predetermined quantities of a cleaning fluid, represented in phantom lines in FIG. 14, from the interior of the fluid container 132'. This cleaning fluid may be used to clean or disinfect an operator's hands, wherein the cleaning fluid dispensed through the manual or hand operated dispensing assembly 150 may include any of a variety of different types of hand gels, foams or solutions appropriately formulated for use as a topical application for cleaning the hands of the user. Accordingly the various embodiments of the cleaning assembly 10 of the present invention demonstrate additional versatility through the possible provision of the disinfecting assembly or station 170 and release element 172 located on the housing in a readily accessible and convenient location. As such, users of the cleaning assembly 10 may use the disinfecting station 170 to clean, disinfect, etc. their hands, before and/or after use of the cleaning assembly 10.

As set forth above, the various structural and operative components of the cleaning assembly of the present invention may vary depending on the practical application and/or desired operational features. Accordingly, with primary reference to FIGS. 15-17, yet another embodiment of the present invention includes a removable, replaceable cartridge 200 structured to be removably disposed within the housing or casing 12, as described above. The cartridge 200 includes a support or carrier frame 210 which also may vary in structure and be connected to a plurality of operative components of the cartridge assembly 200. In addition, the cartridge assembly 200 may include connecting or mounting structures 212 which facilitate the removable, replaceable securement of the cartridge assembly 212 within the interior of the housing or casing 12. Moreover, as with the cartridge assemblies 100 and 100', as described above, the cartridge assembly 200 may be easily removed, replaced, repaired, refilled, etc. as needed. The cartridge assembly 200 also includes a base 260 secured to the frame 210 or integrally and/or fixedly connected as a part thereof.

Additional structural features of the removable, replaceable cartridge assembly 200 includes a fluid supply assembly generally indicated as 232 and including at least one but preferably a plurality of at least two fluid reservoirs 234 and 234'. Each of the fluid reservoirs 234 and 234' are operatively associated with a dispenser assembly including individual, correspondingly disposed dispenser structures 236 and 238. Each of the dispenser structures 236 and 238 include a dispensing head or nozzle 236' and 238' which may be associated with a pump or other fluid dispensing structure. A dip tube or other access component may be used to communicate directly with the cleaning fluid disposed within the individual fluid reservoirs 234 and 234' or a common supply 232' of the cleaning fluid. As set forth above, structural details of an appropriate pump or like dispenser device as well as the associated dip tube or other dispensing components may be considered the structural and operational equivalent as that used with the preferred embodiments of FIGS. 1-14.

Additional structural features of the removable, replaceable cartridge assembly 200 include the provision of an applicator assembly generally indicated as 240. In this preferred embodiment, the applicator assembly 240 includes a plurality of applicator segments 242 connected to a base 260 and extending outwardly therefrom into the path of travel 30, 31 as described with reference to FIGS. 1 and 10 and into interruptive, engaging relation to the head portion 14 as it moves there along. As with the embodiments of FIGS. 1-14, the housing 12 includes an entrance portion and an exit portion and the path of travel 30 extends there between. The housing 12 and the path of travel are structured to facilitate the swiping motion and movement of the head portion 14 on the interior of the casing and along the path of travel 30 in the direction 31. As set forth above, the cleaning action or cleaning procedure is performed at least on the diaphragm 16 and retaining rim 18, at least in part, by engagement by the applicator assembly 240 and plurality of applicator segments. Further, at least some or more practically at least a majority or all of the plurality of applicator segments 242 are inclined at a sufficiently angular orientation relative to the base 260 so as to provide the intended cleaning action on the engaged portions of the head portion 14, while at the same time serving to remove excess fluid or other unwanted remnants from the diaphragm 16 and retaining rim 18. In one embodiment this inclination is downward towards the base 260 so movement is directed towards the base, however, it is recognized that the inclination could also be downward away from the base 260 so that movement is directed away from the base.

More specifically, the plurality of applicator segments 242 may include an interior channel 243 having a substantially concave, transverse cross-sectional configuration, wherein the interior channel 243 extends along the length of the applicator segments 242 from a front or free end thereof to the exposed surface of the base 260. Moreover, the inclined, angular orientations of the plurality of applicator segments 242 along with the provision of the concave interior recesses 243, will serve to provide a cleaning action on the engaged portions of the head portion 14 and also have a tendency to at least partially remove excess fluid and unwanted remnants from the head portion 14, by directing such remnants away from the engaged surfaces of the head portion 14. As a result, the engaged portions of the head portion 14 will be cleaned and free of unwanted remnants. In order to provide an appropriate an intended cleaning action on the head portion 14, the plurality of applicator segments 242 are formed of a flexible, resilient material which facilitates an at least minimal conforming of each of the applicator segments 242 to the surfaces of the head portion 14 which are engaged thereby. However, the plurality of applicator segments 242 may have at least a minimal amount of semi-rigid characteristics to be "shape stable". As such the applicator segments 242 are able to assume their intended position, orientation and configuration as clearly represented in FIGS. 15 and 16 after engaging and performing a cleaning action on the head portion 14 as it moves along the path of travel 30, 31 on the interior of the housing or casing 12 and along the length of the cartridge 200.

Figure 15:
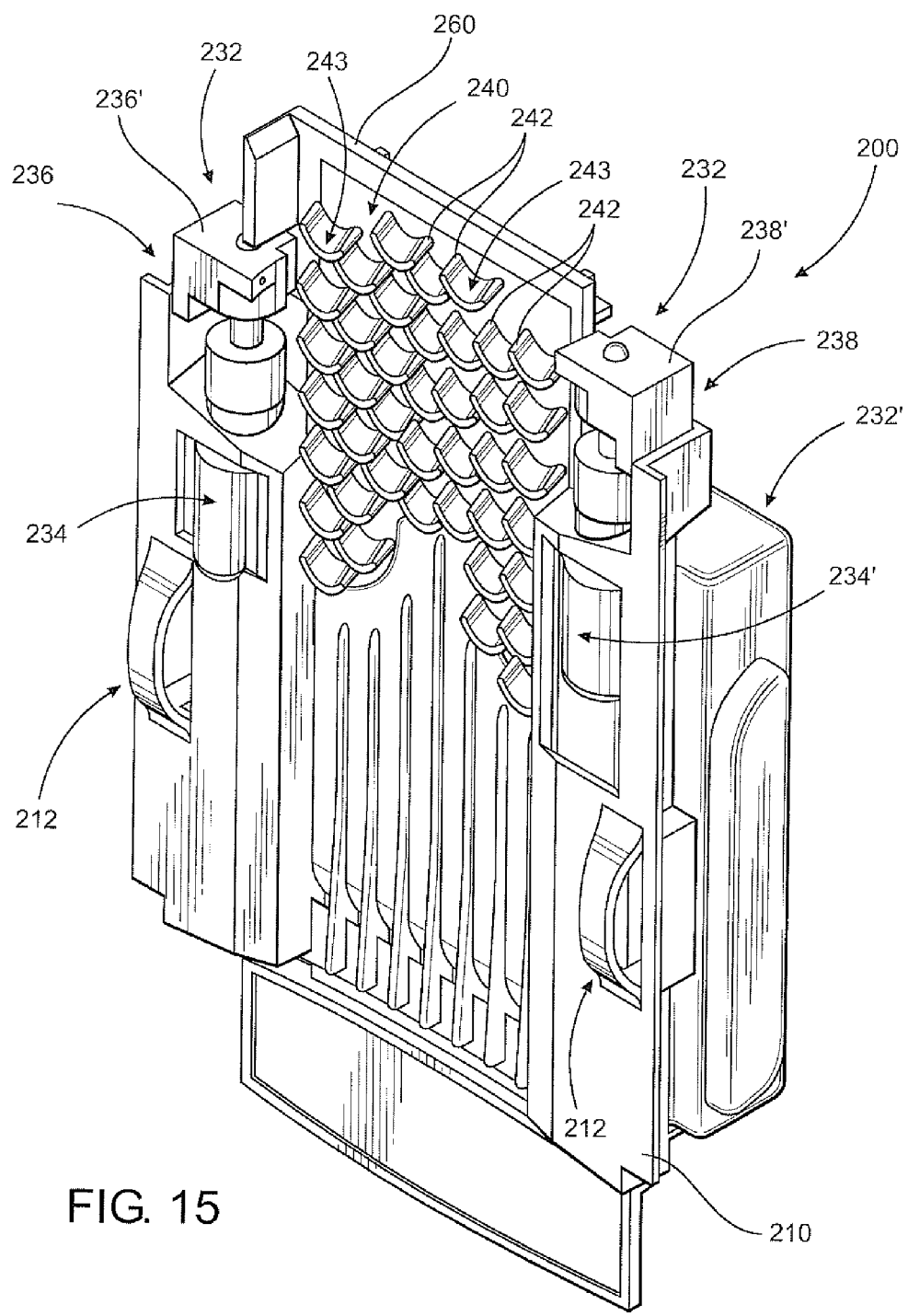
FIG. 15 is a front perspective view of yet another preferred embodiment of a replaceable cartridge assembly structured to be removably mounted within the housing of the cleaning assembly of the present invention.
Figure 16:
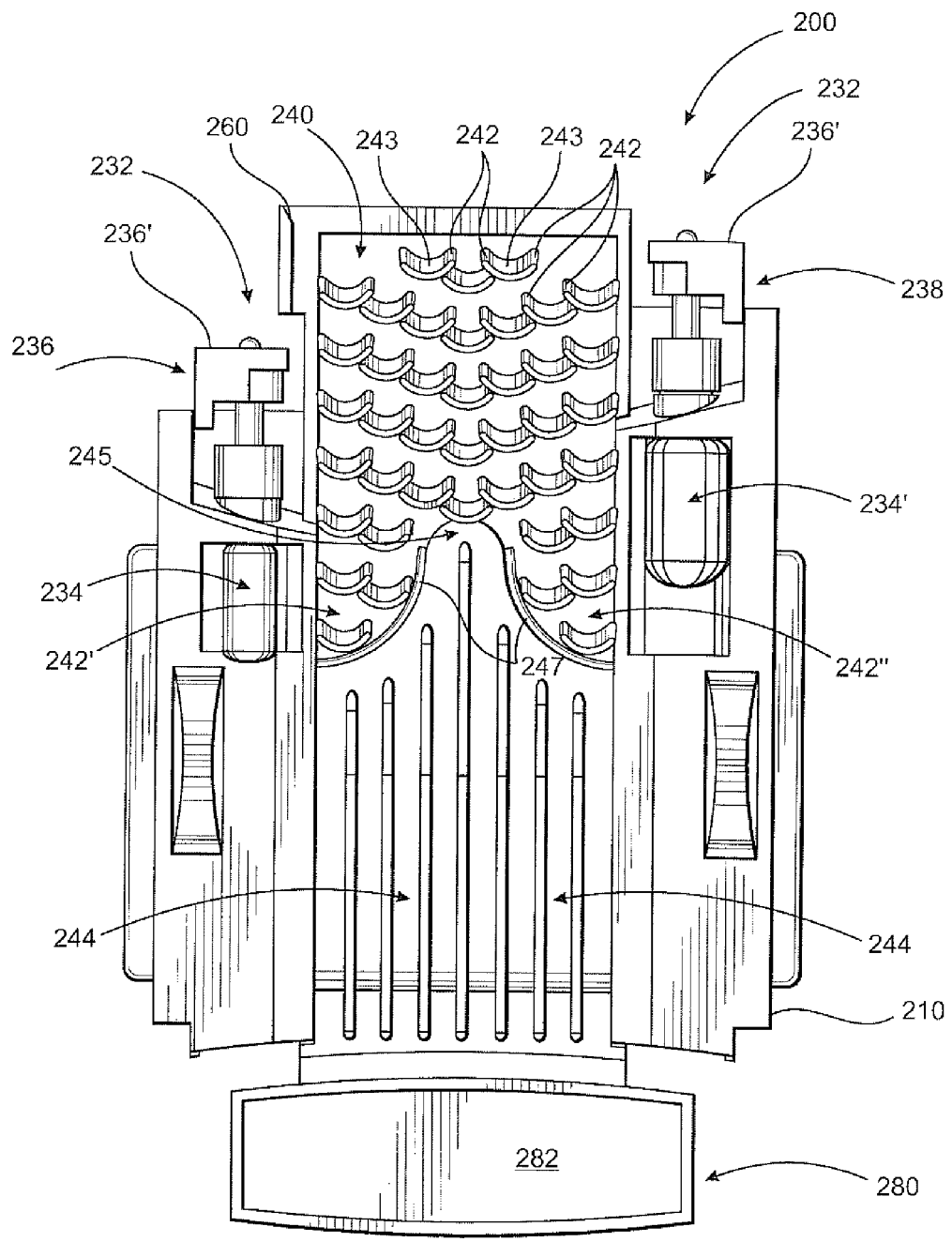
FIG. 16 is a front view of the embodiment of FIG. 15.
Figure 17:
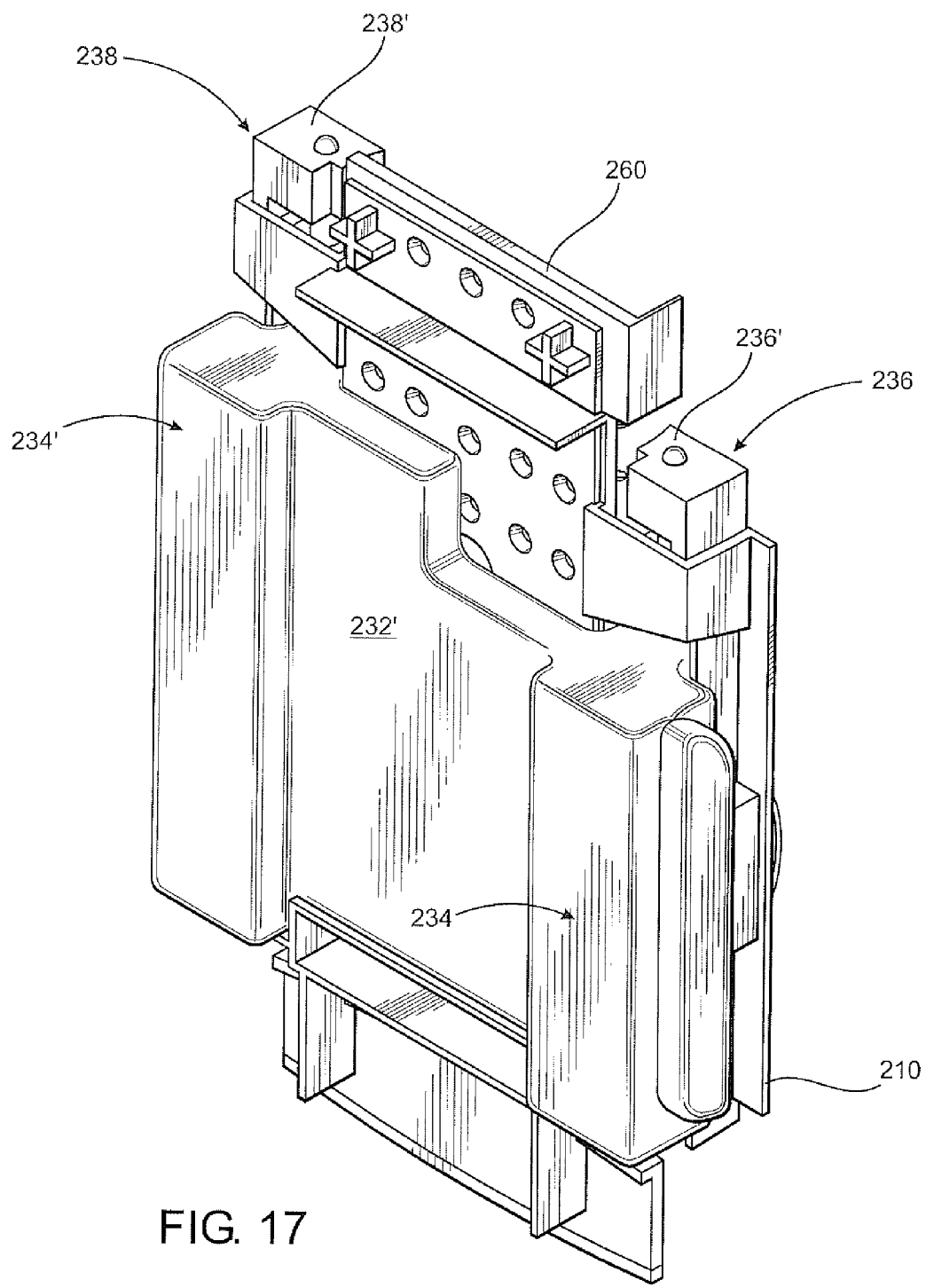
FIG. 17 is a rear view of the embodiment of FIGS. 15 and 16.

In order to engage intended surface portions of the head portion 14 and perform the intended cleaning action on at least the diaphragm 16 and retaining rim 18, the plurality of applicator segments 242 are arranged in a predetermined array, which could be random or symmetric. One embodiment of such a predetermined array is represented in FIGS. 15 and 16 and comprises the plurality of applicator segments 242 being spaced laterally as well as longitudinally from one another, respectively along the width and length of the base 260. As should be apparent, the terms "width" and "length", when referring to the base 260, is meant to describe lateral and longitudinal dimensions of the base 260, when the cartridge assembly 200 is in the operative orientation as represented in FIGS. 15-17. Accordingly, the predetermined array of the plurality of applicator segments 242, as well as the structure, disposition and orientation thereof, facilitate both the application and a partial removal of the cleaning fluid relative to the engaged portions of the head portion 14 as it moves along the path of travel 30, 31. Therefore, the predetermined array of the plurality of applicator segments 242 also includes spaced apart groupings of applicator segments, as at 242' and 242", separated by an extended panel portion 245, as represented in FIG. 16. It is emphasized that the structure, disposition, dimensions and/or configurations of the predetermined array, as well as that of the components of which it is comprised, may vary from that represented in the embodiment of FIGS. 15 and 16. However, common to a plurality of the various structural modifications which may define the different possible predetermined arrays is the ability to remove excess fluid from the diaphragm 16 and retaining rim 18, while leaving at least a thin film or coating of cleaning fluid thereon. Again, the coating or film of cleaning fluid remaining on the head portion 14 should not be excessive in quantity but still sufficient to further facilitate the disinfection of the head portion 14 after it passes from the path of travel 30, 31 and out of the housing 12, where the film or coating naturally evaporates. Therefore, as the head portion 14 passes along the path of travel 30, 31, it will engage at least some of the plurality of applicator segments 242 which will perform the aforementioned cleaning action on the engaged surfaces thereof. Thereafter, as the head portion 14 reaches the extended portion 245 of the panel 244, a substantially centrally located portion of the diaphragm 16 and retaining rim 18 will pass from and beyond any of the applicator segments 242 and pass over, but not necessarily engage, the extended portion 245 of the panel 244. However, the lateral or side portions of the diaphragm 16 and retaining rim 18 will engage the spaced apart groupings 242' and 242" of the applicator segments 242, wherein cleaning fluid and cleaning action will still be applied thereto, while facilitating the removal of unwanted remnants from these lateral or side portions. As a result, a coating, film or like quantity of the cleaning fluid will remain on the diaphragm 16 and retaining rim 18 of head portion 14 even after it is removed from the path of travel 30 and the casing 12. The quantity of the remaining coating of the cleaning fluid still present on the diaphragm 16 and/or retaining rim 18 will be such as to evaporate in the normal fashion once the head portion 14 is removed from the casing 12, while still acting to aid in the disinfecting of the head portion 14.

In order to assure removal of excess cleaning fluid while assuring that an at least minimal quantity in the form of the aforementioned coating or film of the cleaning fluid remains on the head portion 14, a skimmer assembly may be provided in at least one preferred embodiment of the present invention. The skimmer assembly of the embodiment of FIGS. 15 and 16 includes a plurality of skimmer structures or members 247, located at the lower or trailing periphery or peripheral end of the array of the plurality of applicator segments 242. These skimmer structures or members 247 will protrude, at least partially into the path of travel 30 and into interruptive relation with the correspondingly disposed surfaces of the head portion 14. Due to the skimmer members 247 protruding outwardly from the base 260 and/or panel 244, they will engage and provide a skimming or "squeegee" action on the engaged, surface portions of the head portion 14. Accordingly, any excess cleaning fluid will thereby be removed from these engaged surfaces, while at least some or even a majority surface of the diaphragm 16 and retaining rim 18 of the head portion 14 maintains at least a thin or minimal quantity in the form of a coating of the cleaning fluid thereon. As set forth above, the remaining coating of cleaning fluid will be sufficient to further facilitate the disinfecting of the head portion 14 and subsequently evaporate, once the head portion 14 is removed from the housing or casing 12.

Additional structural and operative features of the preferred embodiment of the cartridge assembly 200, as represented in FIGS. 15-17, include the dispenser assemblies 236 and 238, including the dispenser heads or nozzles 236' and 238' being disposed in a predetermined relative disposition and orientation relative to one another and to the applicator assembly 240 and path of travel 30. More specifically, the dispenser heads or nozzles 236' and 238' are disposed in a longitudinally offset relation to one another. As represented in FIGS. 15 and 16, dispenser assembly 236 and associated dispenser head or nozzle 236' are located at a lower position along the length of the base 260 and applicator assembly 240 relative to the higher longitudinal position of the dispenser assembly 238 and dispensing header nozzle 238'. Also, similar to the embodiment of FIGS. 7-9, the dispenser assemblies 236 and 238 and there associated dispenser heads or nozzles 236' and 238' are located somewhat "forward" of the applicator assembly 240.

This off-set disposition of the dispenser heads or nozzles 236' and 238', serves to direct the cleaning fluid into the path of travel 30, forward of, but in communicating relation with, the applicator assembly 240 and at different "higher and lower" portions of the path of travel 30 and the applicator assembly 240. As such, the concurrent travel of the head portion 14 along the path of travel will expose it to the cleaning fluid as the cleaning fluid is directed into the path of travel 30, in the manner set forth above. Thereafter, gravity flow of the cleaning fluid, as well as movement of the head portion 14, will serve to at least partially transfer the cleaning fluid onto all or at least the majority of the applicator segments 242 located beneath the actual introduction of the cleaning fluid into the path of travel 30.

Yet additional structural and operative features associated with the cartridge assembly 200 include a display structure generally indicated as 280. The display structure 280 includes a display field 282 connected to the cartridge 200 and more specifically fixedly or removably connected to the frame 210. The display field 282 is more specifically defined by an area of display on which various types of indicia may be disposed. Such indicia may comprise advertising, trademarks, trade names, logos, as well as, or in addition to, instructional or informational displays. As such, the display field or display area 282 is disposed exteriorly of the housing or casing 12 when the cartridge 200 is removably mounted on the interior thereof. The display area or field 282 is thereby clearly visible by users of the cleaning assembly of the present invention and/or others in the vicinity thereof.

While not specifically described with the reference to the preferred embodiment of the removable cartridge assembly 200, the cleaning fluid contained in the individual reservoirs 234 and 234' or a central or common supply 232' may have the same formulation as that described above with the embodiments of FIGS. 1-14. Similarly, activation of the dispenser assembly 236 and 238 is accomplished in the same substantial fashion as represented in the above the embodiments of the above described Figures wherein the dispenser assemblies 236 and 238 are actuated concurrently during and effectively by the passage of the head portion 14 along the path of travel 30 in the direction 31.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. An assembly structured to clean a head portion of a stethoscope, said assembly comprising:
    a housing including an entrance portion and an exit portion and a path of travel for the head portion extending therebetween,
    said entrance and said exit portions respectively structured to facilitate entry and removal of the head portion relative to a housing interior,
    a cartridge assembly disposed within said housing and including a fluid supply assembly connected thereto;
    said fluid supply assembly structured for containment and dispensing of cleaning fluid,
    an applicator assembly including a base; a plurality of applicator segments connected to said base and extending outwardly therefrom into engaging relation with the head portion moving along said path of travel,
    said plurality of applicator segments collectively disposed in predetermined array comprising both a lateral and a longitudinal relative spacing of said plurality of applicator segments,
    said predetermined array configured to apply and at least partially remove the cleaning fluid to and from the head portion,
    an activating assembly movably disposed into and out of actuating relation to said fluid supply assembly,
    a dispenser assembly comprising at least two dispenser structures each operatively connected to said fluid supply assembly and disposed in a sufficiently longitudinal offset relation to one another to concurrently direct cleaning fluid to different portions of said path of travel and in communicating relation to said applicator assembly, and
    said activating assembly structured to activate the dispensing of the cleaning fluid by said dispenser assembly in response to at least said passage of the head portion along said path of travel.

2. An assembly as recited in claim 1 wherein said fluid supply assembly comprises at least two fluid reservoirs, each of said two dispenser structures operatively connected to a different one of said two fluid reservoirs.

3. An assembly as recited in claim 2 wherein said activating assembly comprises a plurality of activating members disposed within said housing, each of said activating members forcibly disposed in activating relation to a corresponding one of said dispenser structures during passage of the head portion along said path of travel.

4. An assembly as recited in claim 1 wherein at least one of said plurality of applicator segments extend outwardly from said base at an inclined orientation relative to said base and in engaging relation to the head portion moving along said path of travel.

5. An assembly as recited in claim 4 wherein said inclined orientation of said plurality of applicator segments is sufficient to direct remnants away from engaged portions of the head portion.

6. An assembly as recited in claim 5 wherein more than half of said plurality of applicator segments extend outwardly from said base at an inclined orientation relative thereto and in engaging relation to the head portion moving along said path of travel.

7. An assembly as recited in claim 6 wherein said more than half of said applicator segments further comprise an interior channel disposed and configured to direct the remnants away from engaged portions of the head portion.

8. An assembly as recited in claim 7 wherein each of said interior channels comprises a substantially concave, transverse cross-sectional configuration extending along a length thereof.

9. An assembly as recited in claim 1 wherein at least one of said plurality of applicator segments include an interior channel configured to direct remnants away from the engaged portions of the head portion.

10. An assembly as recited in claim 9 wherein each of said interior channels comprises a substantially concave, transverse cross-sectional configuration extending along a length thereof.

11. An assembly as recited in claim 10 wherein each of said interior channels are disposed at an inclined orientation relative to said base sufficient to direct remnants away from portions of the head portion engaged by corresponding ones of said plurality of applicator segments.

12. An assembly as recited in claim 1 wherein more than half of said plurality of applicator segments are formed of a flexible, resilient material structured to apply a cleaning action to engaged portions of the head portion.

13. An assembly as recited in claim 12 wherein said flexible, resilient material of said applicator segments is sufficiently semi-rigid to be shape stable.

14. An assembly as recited in claim 1 further comprising a display field connected to said cartridge and including a display area structured to include indicia thereon; said display area disposed in an exposed position on an exterior of said housing.

15. An assembly as recited in claim 1 further comprising a skimmer assembly disposed along said path of travel in interruptive relation to the head portion when moving along said path of travel; said skimmer assembly structured to remove excess cleaning fluid from at least a portion of the head portion.

16. An assembly as recited in claim 15 wherein said skimmer assembly comprises at least one skimmer member disposed at a trailing end of said applicator assembly in engageable relation with corresponding surface portions of the head portion when the head portion is moving along said path of travel.

17. An assembly as recited in claim 16 wherein each of said skimmer assembly comprises a plurality of skimmer members each including a curved configuration extending along a periphery of said array of said plurality of applicator segments.

18. An assembly structured to clean a head portion of a stethoscope, said assembly comprising:
 a housing including an entrance portion, an exit portion and a path of travel for the head portion extending therebetween,
 a cartridge assembly removably disposed within said housing and including a fluid supply assembly connected thereto;
 an applicator assembly including a base and a plurality of applicator segments connected to said base and extending outwardly therefrom into engaging relation with the head portion moving along said path of travel,
 said plurality of applicator segments collectively disposed in a predetermined array comprising both a lateral and longitudinal spacing of said plurality of applicator segments along said base,
 a dispenser assembly including at least two dispenser structures each operatively connected to said fluid supply assembly; and
 said at least two dispenser structures disposed in a sufficiently offset relation to one another to direct cleaning fluid from said fluid supply assembly to different portions of said path of travel and in communicating relation to said applicator assembly.

19. An assembly as recited in claim 18 wherein said two dispenser structures are disposed in a longitudinally offset relation to one another so as to direct cleaning fluid to different longitudinally offset portions of said path of travel and in communicating relation to said applicator assembly concurrently to movement of the head portion along said path of travel.

20. An assembly as recited in claim 19 wherein said fluid supply assembly comprises at least two fluid reservoirs, each of said two dispenser structures operatively connected to a different one of said two fluid reservoirs.

21. An assembly as recited in claim 18 wherein at least one of said plurality of applicator segments extend outwardly from said base at an inclined orientation relative thereto and in engaging relation to the head portion moving along said path of travel; said inclined orientation of said plurality of applicator segments being sufficiently oriented to direct remnants away from engaged portions of the head portion.

22. An assembly as recited in claim 18 wherein more than half of said applicator segments extend outwardly from said base at an inclined orientation and in engaging relation to the head portion moving along the path of travel, said more than half of said plurality of applicator segments being sufficiently angularly oriented to direct remnants away from engage portions of the head portion and comprising an interior channel including a substantially concave, transverse cross-sectional configuration extending along the length of said channel.

23. An assembly as recited in claim 22 wherein each of said interior channels are disposed at an inclined orientation sufficient to direct remnants away from portions of the head portion engaged by corresponding ones of said plurality of applicator segments.

24. An assembly as recited in claim 23 wherein more than half of said plurality of applicator segments are formed of a flexible, resilient material structured to apply a cleaning action to engaged portions of the head portion.

25. An assembly as recited in claim 18 further comprising a skimmer assembly disposed along said path of travel in interruptive relation to the head portion when moving along said path of travel; said skimmer assembly structured to only remove excess cleaning fluid from correspondingly disposed surfaces of the head portion.

26. An assembly as recited in claim 25 wherein said skimmer assembly comprises at least two spaced apart skimmer members disposed at a trailing end of said applicator assembly in engageable relation with opposite lateral side portions of the head portion moving along said path of travel.

27. An assembly as recited in claim 18 further comprising a display field connected to said cartridge and including a display area structured to include indicia thereon; said display area disposed in a visually exposed position on an exterior of said housing.

* * * * *